US006610671B2

(12) United States Patent
Buchanan et al.

(10) Patent No.: US 6,610,671 B2
(45) Date of Patent: Aug. 26, 2003

(54) CYCLODEXTRIN SULFONATES, GUEST INCLUSION COMPLEXES METHODS OF MAKING THE SAME AND RELATED MATERIALS

(75) Inventors: Charles M. Buchanan, Kingsport, TN (US); Steven N. Falling, Kingsport, TN (US); Juanelle L. Lambert, Gray, TN (US); Shannon E. Large, Blountville, TN (US); Jozsef Szejtli, Budapest (HU); Lajos Szente, Budapest (HU); Laszlo Jicsinszky, Budapest (HU)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/042,306

(22) Filed: Jan. 11, 2002

(65) Prior Publication Data

US 2002/0128468 A1 Sep. 12, 2002

Related U.S. Application Data

(60) Provisional application No. 60/261,020, filed on Jan. 11, 2001.

(51) Int. Cl.$^7$ .................. A61K 31/724; C08B 37/16
(52) U.S. Cl. .......................... 514/58; 536/103
(58) Field of Search .............. 536/103; 514/58

(56) References Cited

U.S. PATENT DOCUMENTS

| | | | |
|---|---|---|---|
| 3,426,011 A | | 2/1969 | Parmerter et al. |
| 5,134,127 A | | 7/1992 | Stella et al. |
| 5,162,590 A | | 11/1992 | Fischer et al. |
| 5,376,645 A | | 12/1994 | Stella et al. |
| 5,874,418 A | | 2/1999 | Stella et al. |
| 6,046,177 A | | 4/2000 | Stella et al. |
| 6,479,467 B1 | * | 11/2002 | Buchanan et al. ............ 514/58 |

OTHER PUBLICATIONS

Samuel C. Bright, et al., "Alkane Sulphonate Preparation by the Sulphitation of Long Chain Olefins," *J. Appl. Chem. Biotechnol.*, 1975, pp. 901–912, vol. 25.

Bezhan Chankvetadze, et al., "Enantiomeric resolution of anionic R/S–1,1'–binaphthyl–2,2'–diyl hydrogen phosphate by capillary electrophoresis using anionic cyclodextrin derivatives as chiral selectors," *J. Chromatogr. A*, 1995, pp. 234–237, vol. 704.

Robert Herke, et al., "Addition of Bisulfite to α–Olefins: Synthesis of n–Alkana Sulfonates and Characterization of Intermediates," *JAOCS*, Jan. 1992, pp. 47–51, vol. 69, No. 1.

M.S. Kharasch, et al., "The Peroxide Effect in the Addition of Reagents to Unsaturated Compounds. XVIII. The Addition and Substitution of Bisulfite," *J. Org. Chem.*, 1939, pp. 175–192, vol. 3.

Alain Leydet, et al., "Polyanion Inhibitors of HIV and Other Viruses. 7. Polyanionic Compounds and Polyzwitterionic Compounds Derived from Cyclodextrins as Inhibitors of HIV Transmission," *J. Med. Chem.*, 1998, pp. 4927–4932, vol. 41, No. 25.

Michael J. Martinelli, et al., "Selective monosulfonylation of internal 1,2–diols catalyzed by di–n–butyltin oxide," *Tetrahedron Letters*, 2000, pp. 3773–3776, vol. 41.

Charles J. Norton, et al., "Alkanesulfonate Synthesis. I. Ion Catalysis of Sulfite Radical–Ion Addition to Olefins," *J. Organic Chemistry*, Nov. 1968, pp. 4158–4165, vol. 33, No. 11.

R. J. Tait, et al., "Sulfobutyl Ether β–Cyclodextrin as a Chiral Discriminator for Use with Capillary Electrophoresis," *Analytical Chemistry*, Nov. 15, 1994, pp. 4013–4018, vol. 66, No. 22.

Shigeru Terabe, et al., "Electrokinetic Chromatography With 2–O–Carboxymethly–β–Cyclodextrin as a Moving 'Stationary' Phase," *Journal of Chromatography*, 1985, pp. 211–217, vol. 332.

Kaneto Uekama, et al., "Cyclodextrin Drug Carrier Systems," *Chem. Rev.*, 1998, pp. 2045–2076, vol. 98, No. 5.

Gerhard Wenz, et al., "Synthesis of highly water–soluble cyclodextrin sulfonates by addition of hydrogen sulfite to cyclodextrin allyl ethers," *Carbohydrate Research*, 1999, pp. 153–165, vol. 322.

* cited by examiner

*Primary Examiner*—Kathleen K. Fonda
*Assistant Examiner*—Leigh C. Maier
(74) *Attorney, Agent, or Firm*—Michael J. Blake; Bernard J. Graves, Jr.

(57) ABSTRACT

This invention relates to new cyclodextrin derivatives, processes for producing these cyclodextrin derivatives, and inclusion complexes comprised of the new cyclodextrin derivatives and guest molecules, as well as methods of making such materials and related materials and methods of using the same.

14 Claims, 8 Drawing Sheets

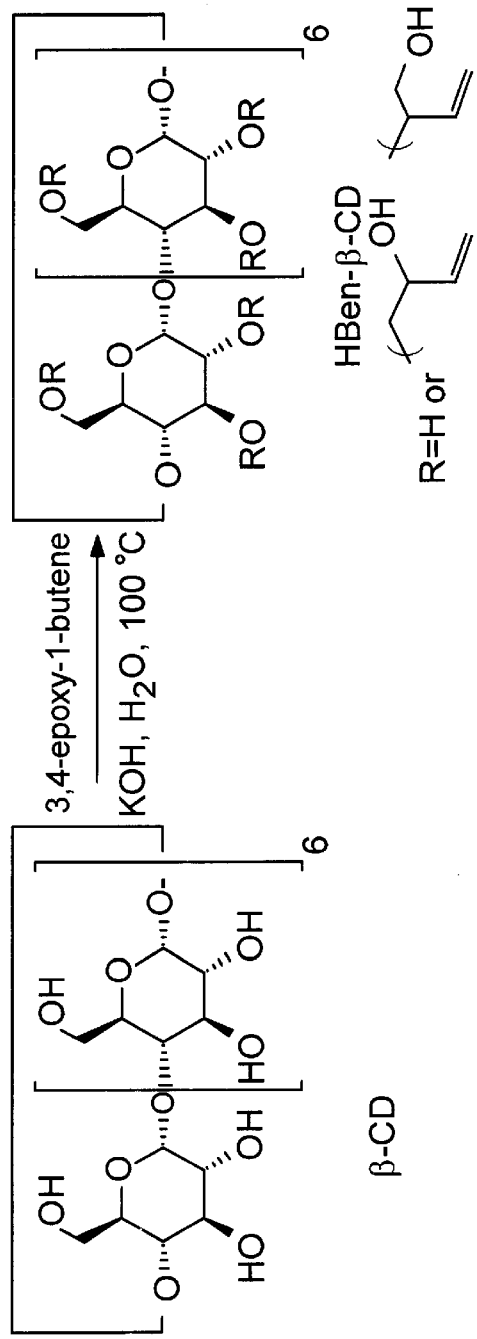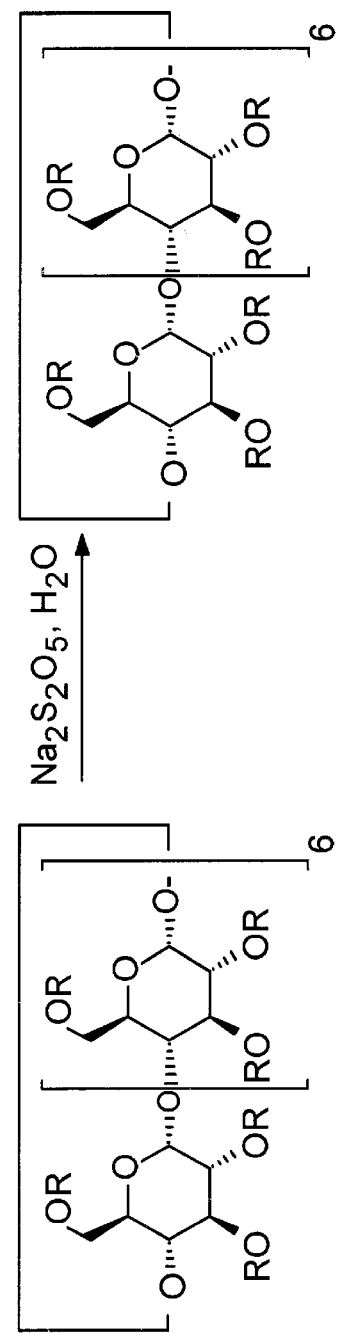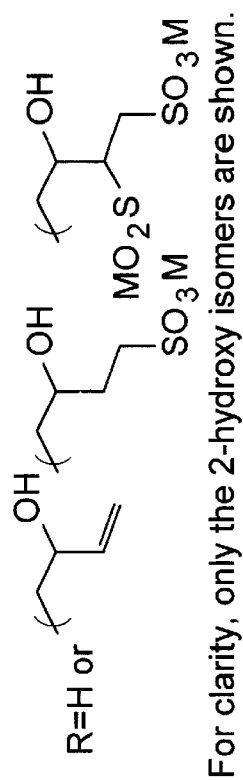
FIG. 1A
FIG. 1B

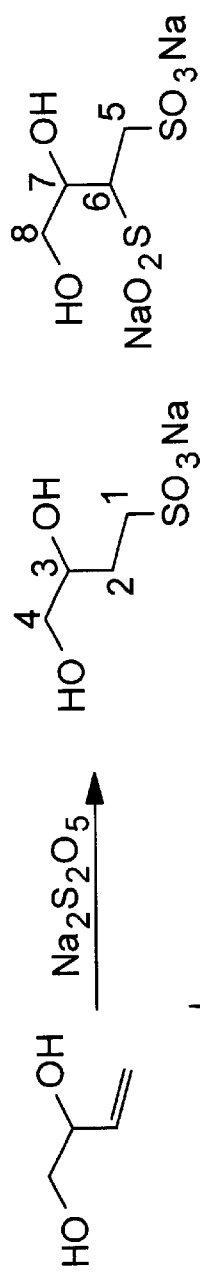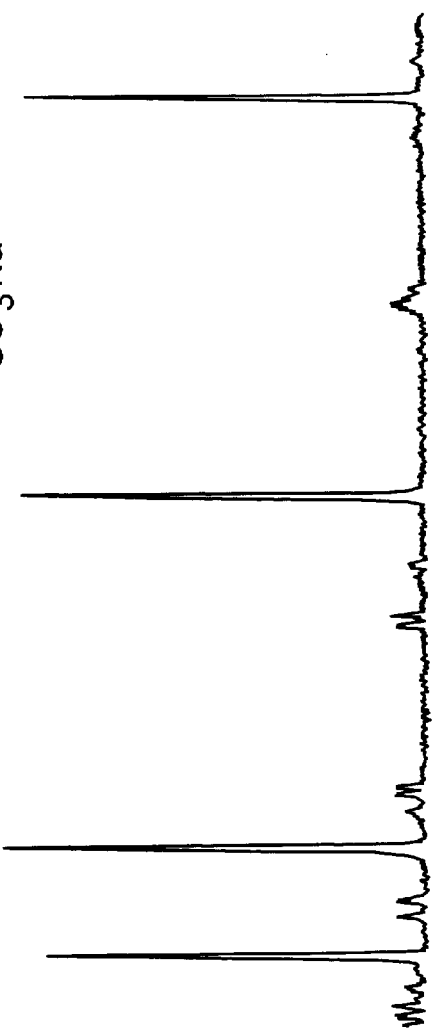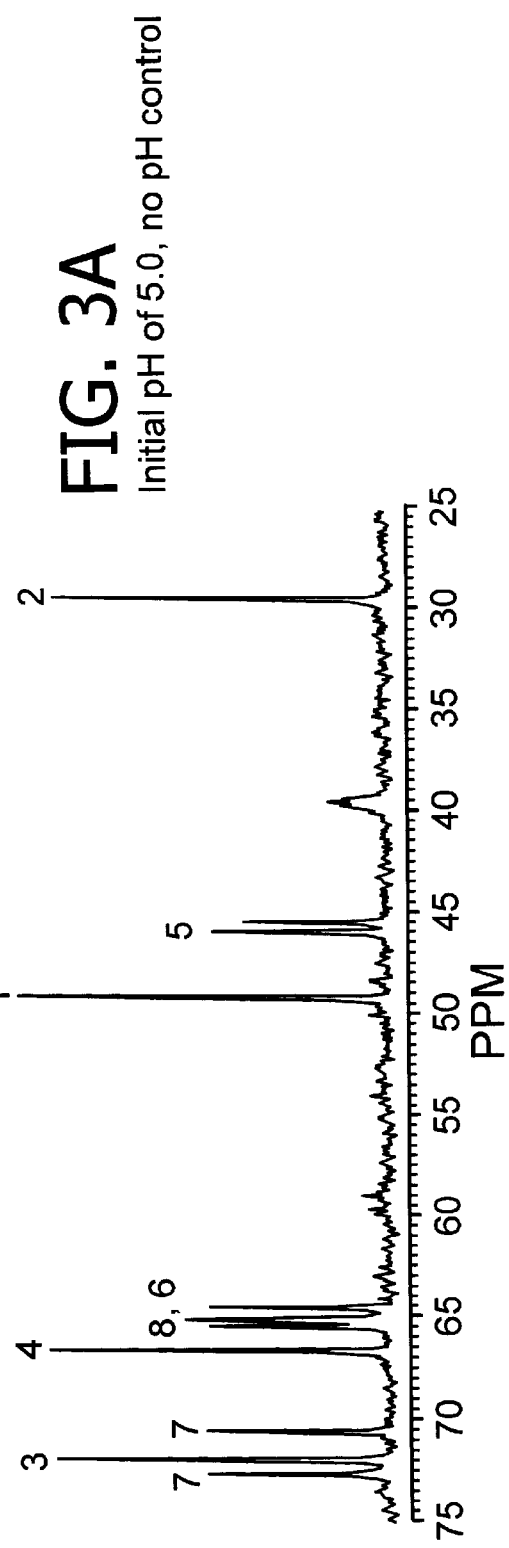
FIG. 3B Controlled at pH 7.3
FIG. 3A Initial pH of 5.0, no pH control

CYCLODEXTRIN SULFONATES, GUEST INCLUSION COMPLEXES METHODS OF MAKING THE SAME AND RELATED MATERIALS

CROSS-REFERENCE TO RELATED APPLICATION

This is a non-provisional application of U.S. Provisional Application No. 60/261,020, filed Jan. 11, 2001; the entire content of which is hereby incorporated by reference.

FIELD OF THE INVENTION

The invention relates to new compositions of matter which comprise sulfonates, sulfonates and sulfinates, or disulfonates of hydroxybutenyl cyclodextrin. The invention further relates to new compositions of matter which comprise sulfonates, sulfonates and sulfinates, or disulfonates of mixed ethers of cyclodextrins where at least one of the ether substituents is hydroxybutenyl cyclodextrin. Other new compositions of matter herein include sodium 3,4-dihydroxybutane-1-sulfonate, a mixture of sodium 3,4-dihydroxybutane-1-sulfonate and at least 5 mol % of disodium 3,4-dihydroxybutane-1-sulfonate-2-sulfinate, and disodium 3,4-dihydroxybutane-1,2-sulfonate. Further new compositions of matter herein include a polysaccharide ether which comprises at least one 2-hydroxybutenyl substituent, wherein the at least one hydroxybutenyl substituent is sulfonated and sulfinated, or disulfonated, and an alkylpolyglycoside ether which comprises at least one 2-hydroxybutenyl substituent, wherein the at least one hydroxybutenyl substituent is sulfonated and sulfinated, or disulfonated. This invention also relates to novel processes for the preparation of the aforementioned novel compositions. This invention further relates to inclusion complexes formed between the sulfonated hydroxybutenyl cyclodextrins and guest molecules. The invention also relates to the use of a sulfonated, sulfonated and sulfinated, or disulfonated cyclodextrin ether which comprises at least one 2-hydroxybutenyl substituent and, optionally, at least one R substituent, wherein R is derived from an O-alkylating agent other than 3,4-epoxy-1-butene. Still further, the invention relates to novel compositions suitable for use as as chiral discriminators in analytical and preparative chromatography.

BACKGROUND OF THE INVENTION

Cyclodextrins (CD) are cyclic oligomers of glucose, which typically contain 6, 7, or 8 glucose monomers joined by α-1,4 linkages. These oligomers are commonly called α-CD, β-CD, and γ-CD, respectively. Higher oligomers containing up to 12 glucose monomers are known, but their preparation is more difficult.

Those skilled in the art of modifying cyclodextrins will understand that there are a number of ways to indicate the extent to which a cyclodextrin molecule has been modified. Each glucose unit of the cyclodextrin has three hydroxyls available at the 2, 3, and 6 positions. Hence, α-cyclodextrin has 18 hydroxyls or 18 substitution sites available and can have a maximum degree of substitution (DS) of 18. Similarly, β- and γ-cyclodextrin have a maximum DS of 21 and 24, respectively.

Often, DS is expressed as an average DS, defined as the number of substituents per glucose monomer. For example, β-CD having a maximum DS of 21 would have an average DS of 3 (21/7=3). As understood by those skilled in the art, the measured DS will relate to the analytical technique utilized. For example, DS by NMR will provide a single value. In contrast, a technique such as MALDI-TOF mass spectrometry will illustrate that these products are, in fact, a mixture of materials with varying degrees of substitution. Such distributions are Gaussian and the DS reported is generally the mean value.

Topologically, CD can be represented as a toroid in which the primary hydroxyls are located on the smaller circumference and the secondary hydroxyls are located on the larger circumference. Because of this arrangement, the interior of the torus is hydrophobic while the exterior is sufficiently hydrophilic to allow the CD to be dissolved in water. This difference between the interior and exterior faces allows the CD to act as a host molecule and to form inclusion complexes with guest molecules (otherwise called an "included material"), provided the guest molecule is of the proper size to fit in the cavity. The CD inclusion complex can then be dissolved in water, thereby providing for the introduction of a sparingly soluble guest molecule into an aqueous environment. This property makes CD inclusion complexes particularly useful in the pharmaceutical, cosmetic and food industries. Reviews of CD inclusion complexes can be found in *Chem. Rev.*, 1997, 97, 1325–1357 and in *Supramolecular Chemistry*, 1995, 6, 217–223.

The production of CD involves first treating starch with an α-amylase to partially lower the molecular weight of the starch, followed by treatment with an enzyme known as cyclodextrin glucosyl transferase which forms the cyclic structure. By conducting the reaction in the presence of selected organic compounds, e.g., toluene, crystalline CD complexes can be formed which facilitate isolation of CD with a predetermined ring size. This process has been extensively reviewed by Szejtli et al., *Compr. Supramol. Chem.*, 1996, 3, 41–56. This process yields the native CD discussed above. Table 1 provides a summary of selected physical properties of cyclodextrins.

TABLE 1

Physical Properties of α-, β-, and γ-CD.

| Property | α-CD | β-CD | γ-CD |
|---|---|---|---|
| No. of Glucose Units | 6 | 7 | 8 |
| MW (anhydrous) | 972 | 1135 | 1297 |
| Solubility (water, g/100 mL, 25° C.) | 14.5 | 1.9 | 23.2 |
| Optical Rotation $\alpha_D$ (H$_2$O) | 150.5 | 162.0 | 177.4 |
| Approximate Cavity Diameter (Angstroms) | 5.2 | 6.6 | 8.4 |

As seen in Table 1, there is an unexpected and marked drop in water solubility for β-CD relative to the α- and γ-CD. This is most unfortunate as β-CD has a highly desirable cavity size that is well suited for forming stable complexes with many pharmaceutically active agents. The β-CD is also the most abundant and lowest cost CD available.

Many investigators have found that the decreased water solubility of β-CD can be overcome somewhat by preparing derivatives with a low DS (typically lower than 7). A CD derivative with a low DS may be preferred for some uses because it has been shown in certain cases that the binding strength of the CD derivative with a pharmaceutical active decreases with increasing DS (Pitha, J., et al., *Int. J. Pharmaceutics*, 1988, 46, 217–222). It has also been shown that even a low level of substitution can substantially increase the water solubility relative to the parent β-CD. However, it should be noted that at a low DS level, some of the CD molecules would not contain a substituent. That is, there will be a distribution of cyclodextrin molecules in a reaction product, depending upon the target DS, in which some of the CD molecules will have no substituents, some will have 1 substituent, some will have 2 substituents, etc.

Substitution of β-CD is a highly desirable phenomenon for some uses. Specifically, unmodified β-CD has been shown to cause renal and liver damage after parenteral administration (Uekama, K., et al., *Chem. Rev.* 1998, 98, 2045–2076). Because of the lack of enzymes specific to β-CD in mammals, it is thought that the cyclodextrin molecules will remain intact after parenteral administration and hence accumulate in the renal tissue. Crystallization of the β-CD or its complexes leads to the observed necrotic damage. Hence, the use of unmodified CD in a clinical setting is generally limited to oral or topical pharmaceutical formulations.

Many neutral and charged CD derivatives are known. The neutral CD derivatives are typically ethers prepared by displacement of halides (U.S. Pat. No. 4,638,058) or by opening of epoxides (U.S. Pat. No. 4,727,064). In special cases, the ether may be polyhydroxylated (European Pat. Publication No. 486445 A2). Methods of ether formation via epoxide opening are disclosed in U.S. Pat. Nos. 3,459,731 and 4,727,064. The preferred epoxides are ethylene oxide (EO) and propylene oxide (PO).

A recent invention by Buchanan et al., U.S. Provisional App. No. 60/203,500, the disclosure of which is incorporated herein in its entirety by this reference, discloses hydroxybutenyl cyclodextrin (HBenCD™) or mixed ethers of HBenCD™ (HBenRCD) as new neutral CD derivatives, processes for the preparation of these new derivatives, and uses for the new CD derivatives (HBenCD is a registered trade name of Eastman Chemical Company).

There are many reports in the prior art related to charged CD derivatives. These charged CD derivatives may be anionic, cationic, or zwitterionic. For example, Parmeter et al. (U.S. Pat. No. 3,426,011 the disclosure of which is herein incorporated by this reference in its entirety) disclose the preparation of anionic cyclodextrins in which the charged group may be any organic acid group such as phosphoric acid, phosphonic acid, phosphinic acid, sulfonic acid, sulfinic acid, or carboxylic acid. Further examples of the preparation of anionic CD derivatives can be found in U.S. Pat. Nos. 5,134,127 and 5,376,645, the disclosure of which is herein incorporated in its entirety by this reference.

The preparation of cyclodextrin allyl ethers and their subsequent conversion to charged cyclodextrin derivatives has been disclosed. For example, Wenz and Hofler (*Carbohydr. Res.* 1999, 322, 153–165) have described the preparation of regioselectively and statistically substituted allyl and 3-allyloxy-2-hydroxypropyl cyclodextrin ethers. In a second example of the preparation of cyclodextrin allyl ethers and their subsequent conversion to charged cyclodextrin derivatives, Leydet et al. have described the preparation of perallylated cyclodextrins and their conversion in two steps to anionic and zwitterionic cyclodextrin derivatives.

SUMMARY OF THE INVENTION

This invention relates to cyclodextrin derivatives, processes for producing these cyclodextrin derivatives, and inclusion complexes comprised of the new cyclodextrin derivatives and guest molecules, as well as methods of making such materials and related materials and methods of using the same.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 1 shows the reaction of (a) β-cyclodextrin with 3,4-epoxy-1-butene resulting in formation of HBen-β-CD and (b) reaction of HBen-β-CD with $Na_2S_2O_5$ to form sulfonated hydroxybutenyl-β-cyclodextrin.

FIG. 3 shows the carbon 13 NMR spectra (125 MHz) of the reaction product obtained by reaction of 3,4-dihydroxy-1-butene with $Na_2S_2O_5$ at (a) an initial pH of 5 with no pH control and (b) at a controlled pH of 7.3.

DETAILED DESCRIPTION OF THE INVENTION

Figure 2:
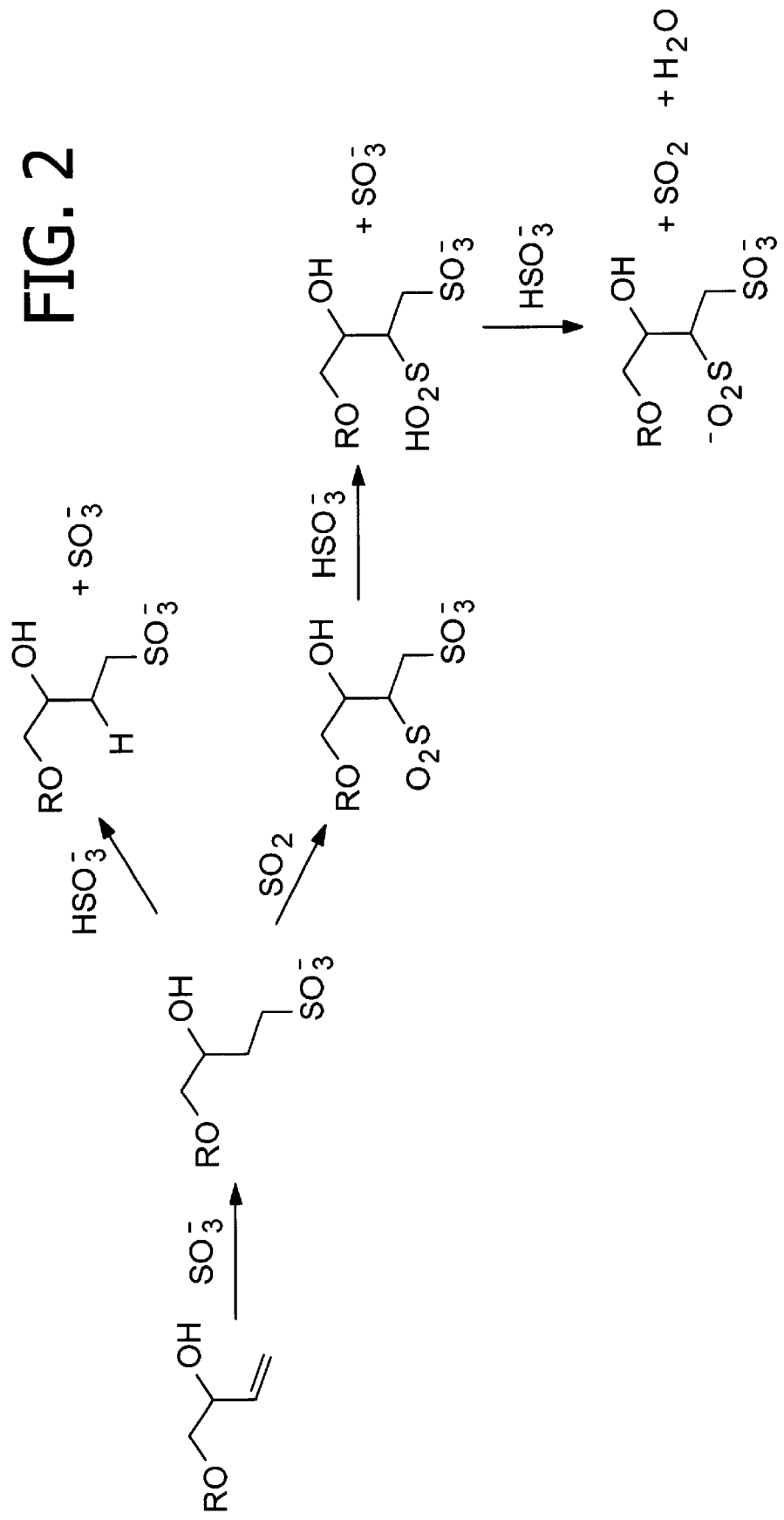
FIG. 2 shows the mechanism by which it is believed that bisulfite adds to double bonds leading to the formation of sulfonates and/or sulfinates.

Before the present compounds, compositions, articles, devices, and/or methods are disclosed and described, it is to be understood that this invention is not limited to specific methods of making or applying the masking compositions herein, or specific compositions thereof, and, as such, may, of course, vary. It is also to be understood that the terminology used herein is for the purpose of describing particular embodiments only and is not intended to be limiting.

It must be noted that, as used in the specification and the appended claims, the singular forms "a," "an" and "the" include plural references unless the context clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

References in the specification and concluding claims to parts by weight of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total dry weight percent of the formulation or composition in which the component is included.

By the term "effective amount" of a compound or property as provided herein it is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

The present invention overcomes many difficulties seen in prior art methods of derivitizing CD by providing a process for the sulfonation of the double bond of HBenCDR or HBenRCD. The sulfonated cyclodextrin ethers herein are previously unknown compositions of matter and the processes of making these compositions of matter are also novel. These new anionically charged cyclodextrin ethers can solubilize and form inclusion complexes with a wide variety of neutral and charged guest molecules. Because of their ability to form inclusion complexes and solubilize sparingly water soluble guest molecules, the new cyclodextrin derivatives may be particularly useful for pharmaceutical, food, and cosmetic applications. Even further, the new cyclodextrin derivatives are useful as chiral discriminators in analytical and preparative chromatography. The inventors herein have also found that the novel processes of the present invention can be extended to other substrates as well, allowing for the formation of other novel compositions, such as sodium 3,4-dihydroxybutane-1-sulfonate, novel sulfonated polysaccharide ethers, and novel sulfonated alkylpolyglycoside ethers.

One aspect of this invention relates to a cyclodextrin ether which comprises at least one 2-hydroxybutenyl substituent in which the at least one hydroxybutenyl substituent is sulfonated (SulfoHBenCD). Another aspect of this invention relates to a cyclodextrin ether which comprises at least one 2-hydroxybutenyl substituent in which the at least one hydroxybutenyl substituent is both sulfonated and sulfinated (SulfoSulfinHBenCD). Yet another aspect of this invention relates to a cyclodextrin ether which comprises at least one 2-hydroxybutenyl substituent and wherein the at least one hydroxybutenyl substituent is disulfonated (DiSulfoHBenCD). This invention further relates to a cyclodextrin ether which comprises at least one 2-hydroxybutenyl substituent and at least one R substituent, wherein R is derived from an O-alkylating agent other than 3,4-epoxy-1-butene and wherein the at least one hydroxybutenyl substituent is sulfonated (SulfoHBenRCD). Additionally, this invention relates to a cyclodextrin ether which comprises at least one 2-hydroxybutenyl substituent and at least one R substituent, wherein R is derived from an O-alkylating agent other than 3,4-epoxy-1-butene and wherein the at least one hydroxybutenyl substituent is both sulfonated and sulfinated (SulfoSulfinHBenRCD). Also, this invention relates to a cyclodextrin ether which comprises at least one 2-hydroxybutenyl substituent and at least one R substituent, wherein R is derived from an O-alkylating agent other than 3,4-epoxy-1-butene, and wherein the at least one hydroxybutenyl substituent is disulfonated (DiSulfoHBenRCD).

In one aspect, the new cyclodextrin ether derivatives of the present invention are derived from hydroxybutenyl cyclodextrin (HBenCD™), which may be prepared from a base-catalyzed reaction between the parent CD and 3,4-epoxy-1-butene (FIG. 1). The cyclodextrin mixed ethers may be similarly prepared from HBenRCD, which may be prepared by reaction of the parent CD with 3,4-epoxy-1-butene and another etherifying agent, either simultaneously or sequentially. Even if not explicitly stated herein, it should be understood that each sulfonate or sulfinate will always have a counterion: proton, alkali metal, or ammonium group (M), specific examples may be potassium or sodium group.

Cyclodextrins useful in the present invention include any cyclic oligomers of glucose joined by $\alpha$-1,4 linkages. The cyclodextrins may be those containing 6, 7, or 8 glucose monomers. In one or more aspects, cyclodextrin may be $\beta$-CD. Mixtures of $\alpha$-CD, $\beta$-CD, and $\gamma$-CD may also be useful in the present invention. In the case of mixtures, the amount of $\alpha$-CD can range from about 1 to about 99 weight %, the amount of $\beta$-CD can range from about 1 to about 99 weight %, and the amount of $\gamma$-CD can range from about 1 to about 99 weight %, where the total amount of CD is 100%. In a further aspect, a mixture may have $\alpha$-CD at from about 10 to about 90 weight %, $\beta$-CD at from about 10 to about 90 weight %, and $\gamma$-CD is at from about 10 to about 90 weight %, where the total amount of CD is 100%.

In the preparation of sulfonated hydroxybutenyl cyclodextrins, a first step may involve the reaction of 3,4-epoxy-1-butene with the parent CD (FIG. 1a). Reaction of the epoxide with the hydroxyl group of the CD may generate a new primary alcohol if the reaction occurs at C3 of 3,4-epoxy-1-butene or a secondary alcohol if the reaction occurs at C4 of 3,4-epoxy-1-butene. One of ordinary skill in the art will recognize that, under basic conditions, reaction with alcohols will normally occur predominately at C4 and, under acidic conditions, at C3 as disclosed previously in U.S. Pat. No. 2,504,082, the disclosure of which is incorporated herein in its entirety by this reference. Such newly generated hydroxyl groups can in turn react with an additional 3,4-epoxy-1-butene. When reaction occurs between the newly formed hydroxyl and 3,4-epoxy-1-butene, the total number of epoxide groups attached to the CD will be greater than the total DS. The total number of epoxide groups is expressed in terms of molar substitution (MS). In accordance with the present invention, the number of double bonds available for sulfonation will generally be established in this step.

In the case of $\alpha$-CD, the DS of hydroxybutenyl may range from about 0.01 to about 18. For $\beta$-CD, the DS of hydroxybutenyl may range from about 0.01 to about 21; and for $\gamma$-CD, the DS of hydroxybutenyl may range from about 0.01 to about 24. In a further aspect, the DS of hydroxybutenyl may range from about 0.02 to about 9.0 for either $\alpha$-CD, $\beta$-CD or $\gamma$-CD. Still further, the DS of hydroxybutenyl may range from about 1.0 to about 7.0 for either $\alpha$-CD, $\beta$-CD or $\gamma$-CD. In a further aspect, the DS of hydroxybutenyl may range from about 5.5 to about 7.0 for either $\alpha$-CD, $\beta$-CD or $\gamma$-CD.

For the cyclodextrin derivatives of the present invention, the total MS and the MS of the individual substituents should be specified. As utilized herein, the MS of each substituent will be designated by subscripts. As an example, Sulfo$_{4.5}$HBen$_{1.5}$-$\beta$-CD means a SulfoHBen-$\beta$-CD having a total MS of 6.0. The MS for sulfonate is 4.5 and the MS for the hydroxybutenyl is 1.5. As a further example, Sulfo$_{4.5}$Sufin$_{0.9}$HBen$_{1.1}$-β-CD means a SulfoSulfinBen-β-CD having a total MS of 6.5. The MS for sulfonate is 4.5, the MS for sulfinate is 0.9, and the MS for hydroxybutenyl is 1.1.

In terms of regioselectivity of the etherification reaction, the hydroxybutenyl ether substituents can be located at specific hydroxyl groups or may be randomly located. For example, in one aspect the hydroxybutenyl ether substituents can be located preferentially at the primary C6 hydroxyls or they can be located preferentially at the secondary C2, C3 hydroxyls of the anhydroglucose monomer. It is also possible for the hydroxybutenyl ether substituents to be located on both the secondary and primary hydroxyls.

It will be understood by those skilled in the art that the most preferred combination of CD type, DS, MS, and regioselectivity depends upon the physical properties needed for a particular application. In this context, a broad combination of CD type, DS, MS, and regioselectivity is contemplated according to the present invention.

It should be understood that the cyclodextrin ethers of the present invention may be comprised of many isomers. However, isolation and characterization of each individual isomer is normally difficult if not impossible. Further, such isolation and characterization is not necessary to accomplish the objectives of the present invention.

In some aspects of this invention, little unreacted cyclodextrin will remain in the reaction mixture. In one aspect, less than about 5 wt % unreacted CD may remain in the reaction mixture after reaction of 3,4-epoxy-1-butene with the CD. In a further aspect, less than about 1 wt % of unreacted CD may remain in the reaction mixture after reaction of 3,4-epoxy-1-butene with the CD. This should be contrasted with U.S. Pat. Nos. 3,426,011, 5,134,127, and 5,376,645, the disclosures of which are incorporated herein in their entireties, each of which allow for considerable amounts of unreacted CD in the reaction mixture (up to 50 wt %).

A further aspect of this invention is a composition of matter based upon mixed ethers of cyclodextrin wherein at least one of the ether substituents is hydroxybutenyl (HBenRCD) and wherein R is derived from an ether substituent other than hydroxybutenyl. Epoxides that can be used in the preparation of mixed ethers of HBenRCD include the lower alkylene oxides such as, for example, ethylene oxide, propylene oxide, butylene oxide, amylene oxide and glycidol. Other epoxides include aryl or halogen substituted alkylene oxides such as styrene oxide or epichlorohydrin. Mixtures of these epoxides can also be utilized in this invention. Preferred lower alkylene epoxides include ethylene oxide and propylene oxide with propylene oxide being the most preferred epoxide. Reaction of these epoxides with CD has many of the same considerations as noted above which 3,4-epoxy-1-butene.

In preparing mixed ethers of CD, it is not necessary that the additional ether groups, R, be derived from reaction of CD with an epoxide. The additional ether groups, R, can be derived from reaction of CD with non-epoxide O-alkylating agents. Appropriate non-epoxide O-alkylating agents may include alkyl-, hydroxyalkyl-, arylalkyl-, carboxyalkyl-, (alkyloxycarbonyl) alkyl-, allyl-, or vinyl-halides, sulfonates or diazomethane. Mixtures of non-epoxide O-alkylating agents can also be utilized. Specific examples of non-epoxide O-alkylating agents include methyl chloride, methyl iodide, methyl bromide, ethyl bromide, propyl bromide, butyl bromide, methyl or ethyl chloroacetic acid, sodium chloroacetate, chloroacetic acid, benzyl bromide, dimethylsulfate, 1-N,N-dialkylamino-2-chloroethane and the like.

In preparing mixed ethers of cyclodextrin wherein at least one of the ether substituents is hydroxybutenyl, the other ether substituents may be added to the CD either by a simultaneous addition of 3,4-epoxy-1-butene and one or more epoxides and/or other O-alkylating agents or by sequential addition of 3,4-epoxy-1-butene and one or more epoxides and/or other O-alkylating agents. Those skilled in the art will recognize that the order of addition of epoxides/O-alkylating agents can impact substitution patterns and, hence, physical properties.

Methods for preparing HBenCD™ or HBenRCD have been disclosed in U.S. Provisional App. Ser. No. 60/203,500 and are incorporated herein in its entirety.

In the preparation of the sulfonated cyclodextrin ethers of the present invention, a second step may involve the radical addition of bisulfite ($HSO_3^-$) to the double bonds of hydroxybutenyl cyclodextrin to introduce the sulfonate groups (FIG. 1b). For convenience, the $HSO_3^-$ is typically provided in the form of $Na_2S_2O_5$ as pyrosulfite anions ($S_2O_5^{2-}$) that are in thermodynamic equilibrium with $HSO_3^-$ in aqueous solution.

As set out above, the number of double bonds available for sulfonation may be established in the initial reaction step leading to the formation of HBenCD™ or HBenRCD. For the SulfoHBenCD or SulfoHBenRCD compositions of the present invention, at least one of the hydroxybutenyl substituents may be sulfonated. It has been discovered according to the invention herein, even the attachment of single sulfonate substituent may lead to an increase in solubility of a CD derivative and its inclusion complexes. Without being bound by theory, it is thought that mutual repulsion of charges may inhibit self-association of the CD derivative. In the case where the number of hydroxybutenyl substituents is from about 0.2 to about 9.0, the DS of sulfonate may be from about 0.2 to about 9.0. In the case where the number of hydroxybutenyl substituents is from about 5.5 to about 7.0, the DS of sulfonate may be from about 1.0 to about 7.0.

Sulfonation of an allylic double bond with a bisulfite radical can lead to the formation of additional products (FIG. 2). For the present invention, one potential additional product is disodium 3-hydroxy-butyl-1-sulfonate-2-sulfinate cyclodextrin (SulfoSulfinHBenCD), which may arise by the addition of $SO_2$ to the radical initially produced by the addition of a sulfite radical anion to the double bond.

In the context of SulfoHBenCD, in one embodiment, less that about 10% of sulfonated hydroxybutyl ether substituents may also be sulfinated. In a further aspect, less than about 5% of sulfonated hydroxybutyl ether substituents are also sulfinated. In a further aspect, no sulfinate may be present.

SulfoSulfinHBenCD is a previously unknown composition of matter. Relative to SulfoHBenCD, HBenCD™, or the parent CD, sulfonation and sulfination may further affect the charge density around the cavity of the cyclodextrin, thereby modifying the solubility of the CD and its complexes, the binding of the CD with a guest molecule, and the toxicity profile of the cyclodextrin. In the present invention involving SulfoSulfinHBenCD, in one aspect, at least about 10% of sulfonated hydroxybutyl ether substituents may also be sulfinated. In a further aspect, from about 15 to about 80% of the sulfonated hydroxybutyl ether substituents may also be sulfinated. Still further, from about 25 to about 60% of the sulfonated hydroxybutyl ether substituents may also be sulfinated.

The sulfinate substituent of SulfoSulfinHBenCD can be further oxidized with readily available commercial reagents such as aqueous hydrogen peroxide or sodium hypochlorite. This normally results in the formation of disodium 3-hydroxybutyl-1,2-sulfonate cyclodextrin (DiSulfoHBenCD), which is a previously unknown composition of matter. As with SulfoSulfinHBenCD, oxidation of the sulfinate may further affect the charge density around the cavity of the cyclodextrin, thereby modifying solubility of the CD and its complexes, the binding of the CD with a guest molecule, and the toxicity profile of the cyclodextrin. In one aspect of the present invention involving DiSulfoHBenCD, at least about 50% of sulfinated substituents may be further oxidized to the sulfonate. In a further aspect, at least about 90% of sulfinated substituents may be further oxidized to the sulfonate.

The addition of hydrogen sulfite to olefins is a well-known reaction that is commonly used in the preparation of alkyl sulfonates (Kharasch, M. S., et al., *J. Org. Chem.* 1939, 3,175–192; Bright, S. C., et al., *J. Appl. Chem. Biotechnol.* 1975, 25, 901–912; Norton, C. J., et al., *J. Org. Chem.* 1968, 33, 4158–4165; Herke, R., et al., *JAOCS,* 1992, 69, 47–51; Fischer, M., U.S. Pat. No. 5,162,590, 1992. As noted above, the addition of bisulfite to allyl ethers has also been reported (*Carbohydr. Res.* 1999, 322, 153–165). The methods described in these reports typically require co-solvents, catalysts, elevated temperature and pressures and may often lead to significant formation of by-products and extended reaction times. As will be detailed, the inventors herein have surprisingly found that in the practice of this invention, co-solvents and catalysts may be necessary. The reactions can be conducted at reduced temperatures. Elevated pressure is also not necessary, thereby generally eliminating the need for a high-pressure autoclave. It has been found herein that by controlling reaction pH and temperature, formation of the sulfinate can be either eliminated or maximized and that reaction times are significantly decreased.

In view of these surprising findings, another aspect of this invention relates to the process for preparing the new compositions of this invention, which comprises contacting HBenCD™ with a source of bisulfite at a pH, temperature, and time suitable to convert HBenCD™ to SulfoHBenCD or SulfoSulfinHBenCD. Under similar reaction conditions HBenRCD can be converted to SulfoHBenRCD or SulfoSulfinHBenRCD. In the preparation of SulfoHBenCD, the pH may be from about 6.5 to about 8.0. In a further aspect, the pH may be from about 7.1 to about 7.6. In a further aspect of the invention, the pH of the aqueous solution of $HSO_3^-$ and the pH of the aqueous solution of the HBenCD may be independently adjusted to the desired reaction pH. The temperature of one solution may be adjusted to the desired reaction temperature and the other solution may then be added to this solution. Alternatively, the solution can be mixed and then heated to the desired reaction temperature. During the course of the reaction, the pH will typically drift to a higher pH and it may be necessary to adjust the pH to the desired pH in order to maintain acceptable reaction rates and to minimize sulfination. In the preparation of SulfoSulfinHBenCD, the pH may be from about 4.0 to about 6.0. Another pH for the reaction may be from about 4.5 to about 5. At this lower pH, the level of sulfination may be increased.

In preparing SulfoHBenCD, the reaction temperature may be from about 50 to about 100° C. The reaction temperature may also be from about 65 to about 85° C. In preparing SulfoSulfinHBenCD, the reaction temperature may be from about 70 to about 110° C. A further reaction temperature may be from about 75 to about 100° C. In both cases, the contact time may be from about 10 to about 1200 min. A further contact time may be from about 60 to about 360 min.

Although a catalyst, such a nitrate salt, can be employed in this transformation, the inventors herein have found that it may not be necessary. In further aspects, it has been found that the addition of catalysts may offer no appreciable benefit.

The mild reaction described above should be contrasted with those previously described in the art. For example, Wenz utilized a high-pressure autoclave to conduct a reaction at a pH of 4.4 at 120–140° C. with $KNO_3$ as a catalyst to convert an allyl double bond to a sulfonate. In one aspect of the process herein for preparing SulfoHBenCD, no catalyst is utilized, the pH (about 7.1 to about 7.6) is neutral and the reaction temperature (about 65 to about 85° C.) is much lower, thus leading to minimal formation of the sulfinate, good product yield, and short reaction times. The lower reaction temperature also means that an autoclave may not generally be required. In a further aspect, no catalyst need be used in the present process, thereby resulting in simpler purification.

It is also important to note that sulfonation of HBenCD according to the methods herein does not require that the HBenCD be isolated prior to reaction with $HSO_3^-$. That is, the reaction product obtained from the reaction of the parent CD with 3,4-epoxy-1-butene in water can be carried directly to the sulfonation step which provides for a significantly more simple process relative to processes which require isolation of the olefin-containing intermediate (*Carbohydr. Res.* 1999, 322, 153–165). In some cases it may be desirable to remove the 3,4-dihydroxy-1-butene that may be formed as a by-product during the reaction of the parent CD with 3,4-epoxy-1-butene prior to the sulfonation step. This may be satisfactorily accomplished by nanofiltration of the reaction mixture through a membrane, such as a cellulose acetate membrane having a molecular weight cutoff of about 500.

The reaction products from the sulfonation step can be purified by many methods well known to those skilled in the art such as extraction, dialysis, nanofiltration, or chromatography. In one aspect of the present invention, the crude product may first be extracted with an organic solvent to remove 3,4-epoxy-1-butene oligomers and other by-products. In a further aspect, solvents for this extraction may be methyl acetate, ethyl acetate, or isopropyl acetate. The salts and other low molecular weight components can then be removed by dialysis or by nanofiltration. In one aspect, separation is by nanofiltration as this both purifies and concentrates the reaction product. The product can then be isolated as a powder by methods such as spray or tray drying. Such methods for purification should be contrasted with those disclosed in U.S. Pat. Nos. 5,134,127 and 5,376,645. As noted above, it is exceedingly useful for some applications that the final reaction product not contain unreacted cyclodextrin particularly when the cyclodextrin is to be utilized for parental administration. By one aspect of this invention, little or no unreacted cyclodextrin will be carried into the purification process. In contrast, with the methods of U.S. Pat. Nos. 5,134,127 and 5,376,645, the disclosures of which are incorporated herein in their entireties, unreacted cyclodextrin must be removed by ion-exchange chromatography which means that the product must be treated two times, once to remove salts and once to concentrate the solution. Aside from the increased cost and inefficiency, those methods have also been found to be unreliable in removing unreacted cyclodextrin.

The processes of this invention used for the preparation of sulfonated hydroxybutenyl cyclodextrins can be used to prepare other new compositions of matter as well. For example, the inventors herein have found that by the process of this invention (control of pH at about 7.1 to about 7.6, temperature about 65 to about 85° C.), 3,4-dihydroxy-1-butene can be quickly sulfonated (4 h) to form sodium 3,4-dihydroxybutane-1-sulfonate with little or no formation of disodium 3,4-dihydroxybutane-1-sulfonate-2-sulfinate. Conversely, a mixture of sodium 3,4-dihydroxybutane-1-sulfonate and disodium 3,4-dihydroxybutane-1-sulfonate-2-sulfinate can be rapidly prepared (about 2 h) at pH less than about 6 and higher temperatures (about 75 to about 100° C.). In this case, the amount of disodium 3,4-dihydroxybutane-1-sulfonate-2-sulfinate may be at least about 10 mol % or, in a further aspect, at least 15 about mol %. As with the cyclodextrins, the sodium 3,4-dihydroxybutane-1-sulfonate and disodium 3,4-dihydroxybutane-1-sulfonate-2-sulfinate mixture can normally be easily converted to the corresponding disulfonate by oxidation of the sulfinate. All of these compounds are novel and may be useful as monomers for polycondensation to form polyesters with ionic groups.

Similarly, polysaccharides containing hydroxybutenyl substituents can be sulfonated by the processes of this invention. Although a broad range of polysaccharides is contemplated according to the invention herein, specific polysaccharides may include cellulose, starch, and hemicellulose obtained by alkaline extraction of plant material. In these cases, the polysaccharide ether may be comprised of at least one hydroxybutenyl substituent where the at least one hydroxybutenyl substituent is sulfonated.

Other novel compositions that can be produced by the methods of this invention include sulfonated hydroxybutenyl alkylpolyglycosides. Alkylpolyglycosides (APG) are typically prepared by an acid catalyzed reaction between monosaccharides (e.g., glucose) and long-chain aliphatic primary alcohols (e.g., n-dodecanol). Alkylpolyglycosides and their preparation are described in U.S. Pat. No. 6,077,945, which is herein incorporated into this application in its entirety. Typically, APG are isolated as a neutral aqueous concentrate. Hence, APG are ideally suited for reaction with 3,4-epoxy-1-butene and sulfonation of the resulting olefin. These novel sulfonated hydroxybutenyl alkylpolyglycosides may be useful as ionic surfactants and emulsifiers.

Another aspect of this invention relates to inclusion complexes comprised of SulfoHBenCD, SulfoHBenRCD, SulfoSulfinHBenCD, SulfoSulfinHBenRCD, DiSulfoHBenCD, or DiSulfoHBenRCD and guest molecules. The novel host molecules of this invention are capable of forming inclusion complexes with both neutral and charged guest molecules. Because of generally enhanced binding due to the charged functional groups, the host molecules of this invention may be particularly well suited for forming inclusion complexes with charged guest molecules. Their utility comes from the fact that these inclusion complexes can exhibit enhanced water solubility or water dispersibility relative to the parent CD and/or hydrophobic guest molecule, thereby providing a means for the introduction of sparingly soluble guest molecules into an aqueous environment and a means for increasing the bioavailability of the guest molecule. Furthermore, complexation of the guest molecule with the host molecule can stabilize and decrease the volatility of guest molecules. The inclusion complexes of this invention can also provide for sustained and controlled release of the guest molecule. For these reasons, the novel cyclodextrin derivatives of this invention may be particularly useful in pharmaceutical, cosmetic, or food applications.

Non-limiting examples of pharmacologically actives agents that may be utilized as guest molecules herein include non-steroidal antirheumatic agents, steroids, cardiac glycosides, anticoagulants, benzodiazepine derivatives, benzimidazole derivatives, piperidine derivatives, piperazine derivatives, imidazole derivatives, triazole derivatives, organic nitrates, prostaglandins, and oligonucleotide antisense agents. Non-limiting examples of preferred pharmacological agents include anti-inflammatory and analgesic agents (e.g. acetylsalicylic acid, sodium diclofenac, ibuprofen, sodium naproxen), anticoagulants (heparin, low molecular weight heparins, aspirin, coumadin, dextran, persantine), antidiabetic agents (glibenclamide), antivirals (3TC, AZT, ddC, loviride, indinavir, nelfinavir, tivirapine, ritonavir, squinavir, ddl, ISIS 14803), antistroke agents (lubeluzole, aptiganel, remacemide), vasodilators (glyceryl trinitrate, isosorbide dinitrate, isosorbide 5-mononitrate, pentaerythritol tetranitrate, amyl nitrate, prostaglandin), anticancer agents (ISIS 3521, ISIS 5132), antidepressants (amitriptyline HCl, clomipramine HCl, fluoxetine, amoxapine butriptyline HCl), antifungal agents (amphotericin, econazole, flucytosine, miconazole nitrate), or antibacterial agents (amoxicillin, cefaclor, cephalexin, sodium flucloxacillin, lincomycin HCl, clindamycin, penicillin). Further non-limiting examples of preferred pharmacological agents include diphenyl hydantoin, adiphenine, allobarbital, amino benzoic acid, amobarbital, ampicillin, anethole, azopropazone, azulene barbituric acid, beclomethasone, beclomethasone dipropionate, bencyclane, benzaldehyde, benzocaine, benzodiazepines, benzothiazide, betamethasone, betamethasone, 17-valerate, bromobenzoic acid, bromoisovalerylurea, butyl-p-aminobenzoate, chloral hydrate, chlorambucil, chloramphenicol, chlorobenzoic acid, chlorpromazine, cinnamic acid, clofibrate, coenzyme A, cortisone, cortisone acetate, cyclobarbital, cyclohexyl anthranilate, deoxycholic acid, dexamethasone, dexamethasone acetate, diazepam, digitoxin, digoxin, estradiol, flufenamic acid, fluocinolone acetonide, flurbiprofen, griseofulvin, guaiazulene, hydrocortisone, hydrocortisone acetate, indican, indomethacin, iodine, ketoprofen, pentobarbital, phenobarbital, progesterone, prostaglandin A, prostaglandin B, prostaglandin E, prostaglandin F, testosterone, vitamin A, vitamin D3, vitamin E, or vitamin K3.

Pharmaceutical formulations useful in the present invention include any formulation in human or veterinary medicine containing the novel inclusion complexes of this invention suitable for administration. The novel complexes can be utilized in solid formulations, oral formulations, parenteral (including intramuscular and intravenous) formulations, ophthalmic preparations, nasal drug delivery, dermal formulations, or rectal formulations.

Non-limiting examples of cosmetic and food guest molecules include fragrances, flavors, or phytosterols. Examples include oils of sandalwood, lemon, Douglas fir, patchouli, strawberry, amyl acetate, vanilla, sitosterol, sitostanol, campestanol, or campesterol. In some aspects, the phytosterol cholesterol-lowering food components (sitosterol, sitostanol, campestanol, and campesterol) may particularly be utilized guest molecules. The phytosterol inclusion complexes may primarily be used in foods but, in certain instances, may also be used in pharmaceutical formulations.

The inclusion complexes prepared according to the present invention may be formed by any manner known in the art. Such complexes may be formed, for example, by the techniques described in *Chem. Rev.*, 1997, 97, 1325–1357 and in *Supramolecular Chemistry*, 1995, 6, 217–223; the contents of which are hereby incorporated by reference. These preformed inclusion complexes can then be included in pharmaceutical, cosmetic, or food formulations as desired. In certain instances it is not necessary to preform the inclusion complex. For example, in solid pharmaceutical formulations for oral administration, a sparingly water soluble pharmaceutical active agent and the novel cyclodextrin derivatives of this invention can be individually incorporated into the unit (e.g. tablets or capsules) dose formulation along with other pharmaceutically acceptable auxiliaries or additives that may be added to promote other features such as disintegration, absorption, permeability, or stabilization. During dissolution of the unit, an inclusion complex forms and the solubility and, hence, bioavailability, of the drug active may thereby be increased. It should also be noted that in these formulations, the novel cyclodextrin derivatives of this invention may also act as osmotic pumps, thereby providing for sustained drug delivery. This form of inclusion complex formation and its use for drug delivery has been disclosed in U.S. Pat. Nos. 5,874,418 and 6,046,177, the contents of which are hereby incorporated by reference.

Another example of when it may not be necessary to preform the inclusion complexes can be found in cosmetic applications. For example, when it is desirable to solubilize or stabilize a fragrance in a liquid, the fragrance and the novel cyclodextrin derivatives of this invention can be individually added to the liquid comprising the cosmetic formulation. The factors which normally drive inclusion complex formation, will also do so in the cosmetic formulation.

The benefits derived from this invention may be obtained by having a molar ratio of cyclodextrin derivative to host molecule of from about 10:1 to about 1:10. In a further aspect, the molar ratio may be from about 1:1 to about 5:1.

Another aspect of this invention relates to the use of the sulfonated hydroxybutenyl cyclodextrins as chiral discriminators in high performance liquid chromatography (HPLC), gas chromatography (GC), capillary electrophoresis (CE), and simulated moving bed chromatography (SMB). The sulfonated hydroxybutenyl cyclodextrins may be utilized in the surface bound form where the CD derivative is bound to the surface of the immobile phase or as mobile phase additives. The sulfonated hydroxybutenyl cyclodextrins of the present invention may be particularly useful in CE and in SMB as mobile phase additives. The use of the sulfonated hydroxybutenyl cyclodextrins as mobile phase additives in SMB may be particularly useful as this method is well suited for separation of enantiomers on an industrial scale. Enantiomeric separation in SMB is believed to be based on a preferred equilibrium interaction or complexation of the sulfonated hydroxybutenyl cyclodextrins with one of the enantiomers. The sulfonated hydroxybutenyl cyclodextrin/enantiomer complex has a different mobility than the uncomplexed enantiomer allowing separation of the two enantiomers.

This invention can be further illustrated by the following examples, although it will be understood that these examples are included merely for purposes of illustration and are not intended to limit the scope of the invention unless otherwise specifically indicated. The starting materials are commercially available unless otherwise described. All percentages are by weight unless otherwise described.

EXAMPLES

Hydroxybutenyl cyclodextrins were assayed using high-pressure liquid chromatography (HPLC). A Hewlett Packard 1100 Liquid Chromatograph with an integrated pump, auto sampler, and diode array detector was utilized. A Sedex Model 55 Evaporative Light Scattering Detector was connected in series with the diode array detector. The diode array detector (UV at 210 nm, 16 nm bandwidth, 8 nm slit) was used for the determination of the key impurities, while the light scattering detector was used for the determination of the hydroxybutenyl cyclodextrin. A Shodex Asahipak GS-220 HQ analytical column (300×7.6 mm, 6$\mu$) with a Shodex Asahipak GS-2G 7B guard column (50×7.6 mm) was employed. The sample injection size was 20 $\mu$L and the mobile phase was 35/65 acetonitrile/water at a flow rate of 0.6 mL/min. Standards and samples were prepared in 50/50 acetonitrile/water.

Determination of the MS and the MS range of hydroxybutenyl cyclodextrins were determined by MALDI-TOF Mass Spectrometry (PerSeptive Biosystems Voyager Elite DE MALDI/Time-of-Flight Instrument). The average MS was determined by a weighted average of the components in the sample. Salt content of the samples was determined using a Philips PW2400 x-ray fluorescence spectrometer with a Cr target tube. The data was analyzed using an Omega Data Systems UniQuant package.

The MS of the sulfonated cyclodextrins and sulfonated 3,2-dihydroxy-1-butene were determined by electrospray mass spectrometry. A sample of material was dissolved at a concentration of 5 mg/mL in 75/25 (v/v) mixture of methanol/water. The solution was introduced directly into the electrospray source using a Harvard Apparatus syringe pump. The negative-ion mass spectrum was collected on a Micromass Platform mass spectrometer. Electrospray ionization typically yields multiple charge states as multiple sodium ions are stripped from the molecule. This particular procedure does not detect those molecules for which sulfonation (or sulfination) had not occurred.

Example 1

Sulfonation of 3,4-dihydroxy-1-butene without pH Control.

In a typical procedure, a 10 mL one-neck round bottom flask was charged with 0.53 g (6 mmol) of 3,4-dihydroxy-1-butene dissolved in 1 mL of deionized water. To this solution was added 1.25 g of $Na_2S_2O_5$ dissolved in 2 mL of deionized water. The initial pH of the reaction mixture was 5.0 and no attempt was made to control the pH. The flask was then placed in a preheated oil bath at 100° C. The reaction was stirred at 100° C. for 2 h at which time thin layer chromatography (tlc) indicated complete disappearance of the 3,4-dihydroxy-1-butene (Rf=0.52, EtOAc). The reaction mixture was concentrated to dryness to yield 1.51 g of a white powder. The sample was then analyzed by NMR spectroscopy. The results from this experiment and other experiments involving the same procedure but conducted at different pH are summarized in Table 2.

TABLE 2

Influence of pH on Sulfonation of 3,4-dihydroxy-1-butene.

| Entry | Reaction pH | Reaction Time (hr) | % Sulfonation[1] | % Sulfination[1] | % Diol[1] | Sulfonate/ Sulfinate |
|---|---|---|---|---|---|---|
| 1 | 5.0 | 2 | 64.2 | 35.8 | 0 | 1.8 |
| 2 | 7.0 | 2 | 77.6 | 17.6 | 4.9 | 4.4 |
| 3 | 9.0 | 19 | 79.1 | 16.4 | 4.5 | 4.8 |
| 4 | 13 | 23 | 0 | 0 | 100 | |
| 5 | 4 h pH 4.0, then 15 h pH 12.0 | 19 | 0 | 0 | 100 | |

[1]Determined by proton NMR.

This example shows that pH has a significant effect on reactivity and the relative amount of sulfonation and sulfination. Below a pH of about 4 and above a pH of about 10, no reaction occurs. The reaction proceeds rapidly at pH 5 and the highest amount of the sulfinate occurs in this pH range. In the pH range of about 7 to about 9, formation of the sulfonate is more preferred. However, the rate of reaction slows as the pH is increased.

Example 2
Sulfonation of 3,4-dihydroxy-1-butene with pH Control.

A 50 mL one-neck round bottom flask was charged with 1.0 g (11.4 mmol) of 3,4-dihydroxy-1-butene dissolved in 2 mL of deionized water. A second solution was prepared by dissolving 2.38 g of $Na_2S_2O_5$ in 5 mL of deionized water. The pH of the $Na_2S_2O_5$ solution was adjusted to 7.3 with 4 M NaOH and 1 M $H_2SO_4$. The flask containing the 3,4-dihydroxy-1-butene solution was then placed in a preheated oil bath at 65° C. To the 3,4-dihydroxy-1-butene solution was added the $Na_2S_2O_5$ solution dropwise (addition time=8 min). The reaction was stirred at 65° C. During the course of the reaction, the pH was observed to drift to a higher pH. The pH of the reaction solution was readjusted to 7.1–7.3 by the addition of 1 M $H_2SO_4$. After 4 h, thin layer chromatography indicated disappearance of the 3,4-dihydroxy-1-butene. The reaction was concentrated to dryness to yield 4.6 g of a white powder. The sample was then analyzed by NMR spectroscopy, which revealed that all of the starting material was consumed resulting in the exclusive formation of sodium 3,4-dihydroxybutane-1-sulfonate. No disodium 3,4-dihydroxybutane-1-sulfonate-2-sulfinate was found in the crude reaction product. When the same procedure was employed but at higher temperatures (75, 85, 100° C.), the product was again found not to contain disodium 3,4-dihydroxybutane-1-sulfonate-2-sulfinate. To illustrate, FIG. 3 compares the carbon 13 NMR spectra of the product obtained with no pH control (Example 1, entry 1) to the product obtained with pH control.

In this example, the $Na_2S_2O_5$ solution is added to the 3,4-dihydroxy-1-butene solution and the pH of the reaction media is maintained at 7.3 using $H_2SO_4$. Under these conditions, formation of disodium 3,4-dihydroxybutane-1-sulfonate-2-sulfinate is minimized.

Example 3
Preparation of Sodium 3,4-dihydroxybutane-1-sulfonate.

To a 3000-mL, four-neck, Morton flask equipped with a mechanical stirrer, pH probe, condenser, addition funnel, thermocouple, gas dip tube and heating mantle was added 190.2 g (1.001 mole) of sodium metabisulfite and 640 mL of water. The pH 3.9 solution was adjusted to 7.1 by the addition of 136 g (1.70 mole) of 50% aqueous sodium hydroxide. Air was introduced into the headspace of the flask. The mixture was heated to 55° C. and stirred rapidly to introduce air into the solution. Two moles (176.2 g) of 3,4-dihydroxy-1-butene were added over three hours at 55–56° C. while controlling the pH of the solution at 7.3 to 7.6 by the periodic addition of sulfur dioxide via the gas dip tube. The reaction was continued until the pH stopped drifting (five hours total). NMR showed complete sulfonation of the olefin. The product solution was concentrated to a give a milky white mixture by rotary evaporation at 60° C. and 10 mm. This mixture was diluted with an equal volume of methanol then filtered and the solids rinsed with methanol. The filtrate was rotary evaporated at up to 60° C. and 10 mm to give a white, waxy solid (467.9 g). The solid was dissolved in 468 g of water to give a clear solution of sodium 3,4-dihydroxybutane-1-sulfonate.

$^1$H NMR ($D_2O$): 1.8–2.0 (2 m, 2H, C$\underline{H}_2$CH$_2$SO$_3$Na), 3.0 (m, 2H, CH$_2$C$\underline{H}_2$SO$_3$Na), 3.5–3.6 (2m, 2H, CHOHC$\underline{H}_2$OH), and 3.8 ppm (m, 1H, C$\underline{H}$OHCH$_2$OH). $^{13}$C NMR ($D_2O$): 30.2 ($\underline{C}H_2CH_2SO_3Na$), 49.9 ($CH_2\underline{C}H_2SO_3Na$), 67.5 (CHOH $\underline{C}H_2OH$), and 72.7 ppm ($\underline{C}HOHCH_2OH$).

This example illustrates that the addition of the olefin to the $Na_2S_2O_5$ solution coupled with pH control using $SO_2$ leads to the formation of sodium 3,4-dihydroxybutane-1-sulfonate and minimal formation of disodium 3,4-dihydroxybutane-1-sulfonate-2-sulfinate.

Example 4
Preparation of a Mixture of Sodium 3,4-dihydroxybutane-1-sulfonate, Sodium 1,4-dihydroxybutane-2-sulfonate, and Sodium Sulfonated Oligomers of 3,4-epoxy-1-butene.

To a 3000 mL, four-neck Morton flask equipped with a mechanical stirrer, condenser, addition funnel, thermocouple, and heating mantle was added 180 mL of water and 6 drops of concentrated sulfuric acid. The mixture was heated to 54° C. then 140.2 g (2.00 moles) of 3,4-epoxy-1-butene were added over 90 minutes at 54–57° C. The mixture was slowly heated to 80° C. over two hours then cooled and sampled. Analysis by gas chromatography showed 75% 3,4-dihydroxy-1-butene, 6.6% 1,4-dihydroxy-2-butene, and 18.5% dimers and higher oligomers of 3,4-epoxy-1-butene. The reaction solution was transferred to an addition funnel for use in the next step. The above reaction flask was modified to include a pH probe and gas dip tube. To the flask was added 190.1 g (1.00 mole) of $Na_2S_2O_5$ and 500 mL of water. After the solids were dissolved, 50% sodium hydroxide was added to give a pH of 7.1 (136.0 g, 1.70 moles). Air was introduced into the headspace of the flask. The mixture was heated to 55° C. and stirred rapidly to introduce air into the solution. The above aqueous solution of diols was slowly added to the flask over about two hours at 52–57° C. The pH of the solution was controlled at 7.1 to 7.6 by the periodic addition of sulfur dioxide via the gas dip tube. The reaction was continued until the pH stopped drifting (about five hours total). NMR showed complete sulfonation of olefins. The mixture was concentrated to a give a milky white mixture by rotary evaporation at 40° C. and 18 mm Hg. This mixture was diluted with 500 mL of methanol then filtered and the solids rinsed with 1000 mL of methanol. The filtrate was concentrated at 60° C. and 10 mm Hg to give a white, waxy solid (362.3 g). The solid was dissolved in 362 g of water to give a clear solution of sodium sulfonated diols and oligomers.

This example illustrates that 3,4-epoxy-1-butene can be converted to a mixture of diols and oligomers by acid catalysis which can then be sulfonated by the process of this invention. The mixture of sulfonated diols and oligomers are useful for preparing polyesters.

Example 5
Preparation of Hydroxybutenyl-β-cyclodextrin (HBen-β-CD).

Water (400 mL), β-cyclodextrin (280 g, 0.25 moles) and KOH (3.46 g, 0.062 moles) were charged to a pressure reactor and heated to 100° C. with stirring. 3,4-Epoxy-1-butene (140.2 g, 2.0 moles) was charged to the reaction vessel over a period of 35–45 minutes increasing the reactor pressure in the reaction vessel by 1.5 bar. 3,4-Epoxy-1-butene was quickly consumed as evidenced by the vapor pressure decreasing to pre-addition levels within 15 minutes. The reaction mixture was held at 100° C. for an additional 1 hour to ensure complete reaction. The reaction mixture was allowed to cool to below 50° C. and was neutralized with HCl. Extraction of the aqueous layer with ethyl acetate removed reaction by-products. Co-evaporating the water with ethanol provided the product as off-white crystals in 80–85% yield. The final product was dried in a vacuum oven at prior to characterization by MALDI-TOF mass spectrometry, HPLC and elemental analysis. Following this general procedure, six samples were prepared and their analyses are summarized in Table 3.

TABLE 3

Summary of analyses of HBen-β-CD

| Sample | Wt. % Assay[1] | Wt. % Butenediol[1] | Average MS[2] | MS Range[2] | Wt. % KCl[3] |
|---|---|---|---|---|---|
| 1 | 95.4 | 3.9 | 6.02 | 2–10 | 1.10 |
| 2 | 94.2 | 3.2 | 6.28 | 2–10 | 0.97 |
| 3 | 95.6 | 2.9 | 6.37 | 1–11 | 0.98 |
| 4 | 94.15 | 2.8 | 6.47 | 2–10 | 1.05 |
| 5 | 94.8 | 2.7 | 5.72 | 2–10 | 1.05 |
| 6 | 102.5 | 3.1 | 6.6 | 2–11 | 1.08 |

[1]By HPLC. [2]By MALDI-TOF Mass Spectrometry. [3]By Elemental Analysis.

Example 6
Preparation of Hydroxybutenylated-α-cyclodextrin (HBen-α-CD).

Water (400 mL), α-cyclodextrin (280 g, 0.29 moles) and KOH (4.10 g, 0.25 moles) were charged to a pressure reactor and heated to 100° C. with stirring. 3,4-Epoxy-1-butene (162.6 g, 2.32 moles) was pumped into the reaction vessel over a period of 35–45 minutes, increasing the reactor pressure by approximately 1.5 bar. 3,4-Epoxy-1-butene was quickly consumed with the reactor pressure falling to pre-addition levels within 15 minutes. The reaction mixture was held at 100° C. for 1 hour to ensure complete reaction. The heat source was removed and the reaction mixture was allowed to cool to below 50° C. The reaction mixture was neutralized with HCl. This solution was extracted with ethyl acetate at 70° C. to remove by-products of the reaction. Co-evaporating the solvent with ethanol provided the product as off-white crystals in 80–85% yield. Once isolated, the final product was dried in a vacuum oven at 50° C. for 72 hours prior to characterization by MALDI-TOF mass spectrometry, by HPLC and by element analysis. Following this general procedure, four samples were prepared and their analyses are summarized in Table 4.

TABLE 4

Analyses of the samples of HBen-α-CD.

| Sample | Wt. % Assay[1] | Wt. % butenediol[1] | Average MS[2] | MS Range[2] | Wt. % KCl[3] |
|---|---|---|---|---|---|
| 1 | 101.5 | 4.0 | 6.01 | 2–10 | 1.06 |
| 2 | 98.3 | 2.7 | 5.61 | 2–10 | 1.38 |
| 3 | 95.8 | 3.2 | 5.05 | 1–10 | 0.62 |
| 4 | 98.3 | 3.4 | 5.41 | 1–10 | 1.15 |

[1]By HPLC. [2]By MALDI-TOF Mass Spectrometry. [3]By Elemental Analysis.

Example 7
Initial Screening of the Effect of Increasing Molar Equivalents of $Na_2S_2O_5$ in the Conversion of HBen-β-CD to Sulfonated HBen-β-CD.

General Procedure: HBen-β-CD containing 2.8 wt % 3,4-dihydroxy-1-butene MS=5.72, 1.6 g, ~0.001 mol) prepared and isolated as described above was dissolved in water (3 mL). Sodium metasulfite ($Na_2S_2O_5$, 0.38 g ~0.002 mol) dissolved in water (1 mL) was added to the HBen-β-CD solution and the pH was adjusted to approximately 7 with sodium hydroxide solution. The reaction mixture was immersed into a pre-heated (150° C.) oil bath and stirred for one hour with no control of pH. After 1 h, the water was allowed to evaporate. The obtained solid (1.9 g) was suspended in 96% EtOH (16 mL) and the solids were isolated by filtration and washed with 96% EtOH (3×2 mL). The product was dried under vacuum at room temperature (25–27° C.) in the presence of phosphorous pentoxide. Yield=1.5 g. Table 5 summarizes the experiments preformed using this procedure.

TABLE 5

The molar equivalents of $Na_2S_2O_5$ used in initial screening of the conversion of HBen-β-CD to sulfonated HBen-β-CD.

| Entry | Equivalents $Na_2S_2O_5$ (Molar)[1] | Catalyst | Yield (g)[2] | Approximate Inorganic Salt Content (wt %) |
|---|---|---|---|---|
| 1 | 2.0 | None | 1.5 | 10 |
| 2 | 4.0 | None | 2.1 | 10 |
| 3 | 6.0 | None | 2.6 | 24 |
| 4 | 8.0 | None | 3.1 | 32 |
| 5 | 7.0 | $KNO_3$ | 3.0 | 25 |

[1]The number of equivalents are based on moles of HBen-β-CD. Hence for entry 3, 6 molar equivalents of $Na_2S_2O_5$ based on HBen-β-CD were used or ca. 1 molar equivalents based on double bonds available for sulfonation.
[2]Some water may be retained in the solid product.

Figure 4:
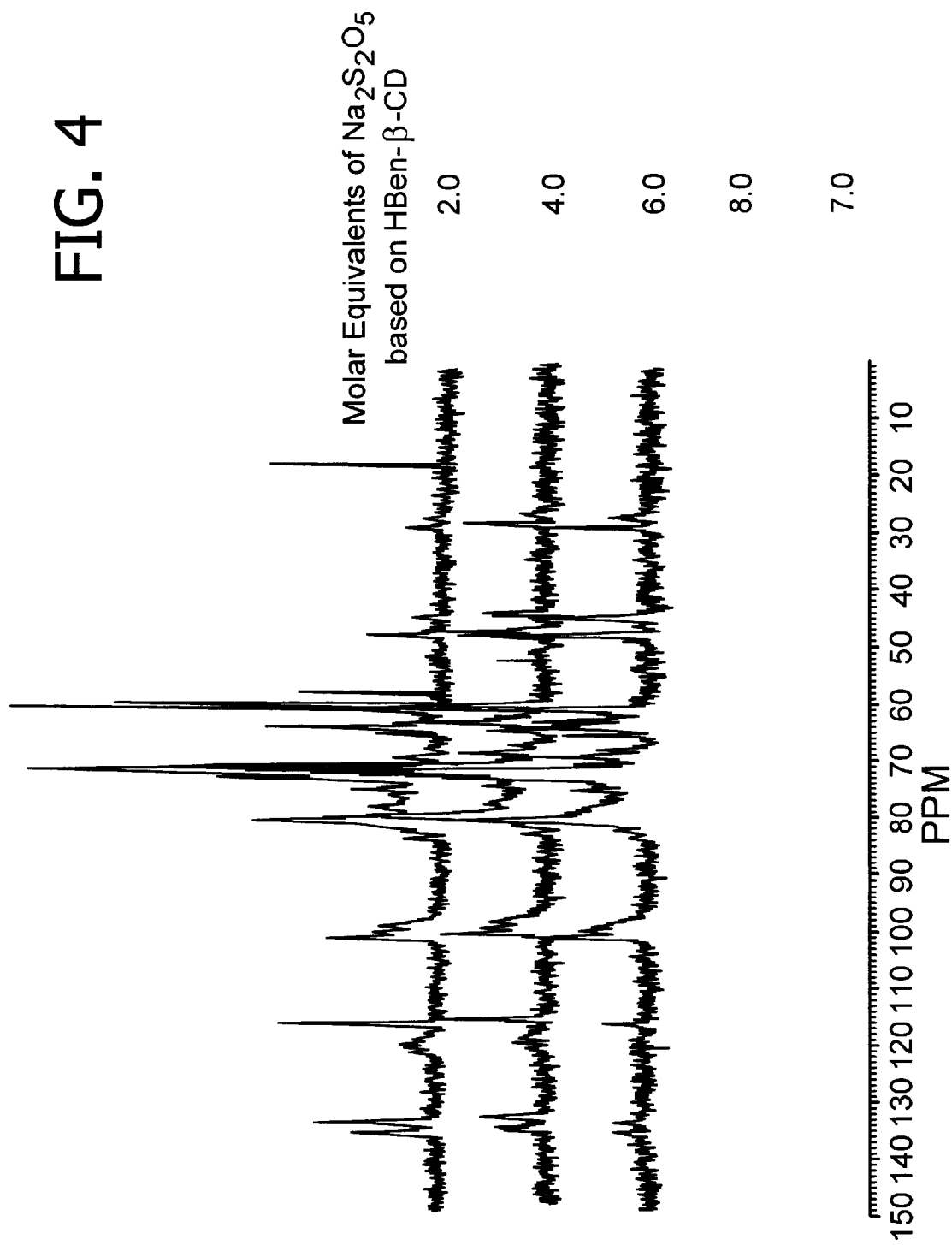
FIG. 4 shows the 100 MHz carbon 13 NMR spectra of sulfonated hydroxybutenyl-β-cyclodextrin prepared from HBen-β-CD using different amounts of $Na_2S_2O_5$.

FIG. 4 shows the carbon 13 NMR spectra (100 MHz) of sulfonated HBen-β-CD prepared from HBen-β-CD using different amounts of $Na_2S_2O_5$. As the number of equivalents of $Na_2S_2O_5$ are increased, the intensity of the carbon resonances due to olefinic carbons (115–140 ppm) decreases giving rise to a new set of resonances at about 29 and 49 ppm which increase in intensity with increasing $Na_2S_2O_5$. The resonances at 29 and 49 ppm arise from the carbons of the newly formed sulfonated side chains. These assignments are based on extensive NMR experiments (2D NMR, INEPT) on both sulfonated 3,4-dihydroxy-1-butene and sulfonated HBen-β-CD.

This example shows that hydroxybutenyl cyclodextrins can be successfully sulfonated using $Na_2S_2O_5$ as the source of bisulfite and that the number of sulfonates can be controlled by the number of double bonds available for sulfonation and by the number of equivalents of $Na_2S_2O_5$ used in the sulfonation reaction.

Example 8
Purification of Sulfonated HBen-β-CD by Solubility Differences and Determination of the MS of Sulfonate by Electrospray Mass Spectrometry.

HBen-β-CD (MS=4.54, 1.5 g, 1 mmol, containing 11.9 wt % 3,4-dihydroxy-1-butene) was dissolved in water (3 mL). Sodium metasulfite ($Na_2S_2O_5$, 1.14 g, 6 mmol) dissolved in water (2 mL) was added to the HBen-β-CD solution and the pH was adjusted to a pH of approximately 7 with a 1.0 M sodium hydroxide solution. The reaction mixture was immersed onto a pre-heated (100° C.) oil bath and stirred for 2 h 10 min. The water was removed under vacuum to give 2.6 g of a hygroscopic white solid. Carbon 13 NMR spectroscopy of the crude product confirmed formation of sulfonated HBen-β-CD. The crude product was taken up in 96% EtOH (10 mL) and the suspension was allowed to stir at 80° C. for 1 h. The solids were isolated by filtration. A portion of the solids were washed with 2×5 mL of 96% EtOH and dried at 60° C. under vacuum. The remaining solids were taken up in the minimal amount of hot water and undissolved solids were removed by filtration. The water was removed at 80° C. under vacuum.

Analysis of the crude reaction product and of the purified product by carbon 13 NMR (125 MHz) revealed that slurrying the crude product in EtOH removes some of the sodium 3,4-hydroxybutane-1-sulfonate which arises from sulfonation of the residual 3,4-dihydroxy-1-butene in the HBen-β-CD. Filtration of a concentrated aqueous solution of the EtOH washed reaction product removes more of this contaminant.

In order to determine the MS of sulfonate, the reaction product was examined by electrospray mass spectrometry. By this method of analysis, the MS of sulfonate was found to be 3.8 and the MS of hydroxybutenyl was found to be 0.7 giving a total MS of 4.5 ($Sulfo_{3.8}HBen_{0.7}$-β-CD).

This example demonstrates the formation of sulfonated hydroxybutenyl cyclodextrin and partial purification of the reaction product on the basis of solubility.

Example 9
Determination of the Charge Distribution in Sulfonated HBen-β-CD by Capillary Electrophoresis.

A randomly substituted hydroxybutenyl cyclodextrin consists of a large number of different isomers. Sulfonation of the double bond of hydroxybutenyl cyclodextrin increases the number of potential isomers. Hence it is extremely difficult to separate all of the isomers by any known technique. However, we have found that it is possible by capillary electrophoresis to separate sulfonated hydroxybutenyl cyclodextrin into characteristic fractions based on the number of charged sulfonate groups.

To illustrate, a sulfonated HBen-β-CD, prepared from HBen-β-CD (MS=5.72) by the method of Example 6 was subjected to capillary electrophoresis using the following conditions:

Apparatus.
Hewlett Packard 3D-CE Capillary Electrophoresis Instrument.
Hewlett Packard 3D-CE Chemstation Software Rev. A. 06.03 [509].
Method.

| | |
|---|---|
| Capillary: | Composite Metal Services Ltd., fused silica uncoated, 50 μm i.d., 375 μm o.d. (TSP 050375), total length 40 cm, length to detector 31.5 cm. |
| Running Buffer: | 20 mM toluene-4-sulfonic acid monohydrate in water, pH 7.6 adjusted with solid tris (hydroxymethyl)-aminomethane. |
| Voltage: | +25 kV. |
| Temperature: | 25 C. |
| Injection mode: | 50 mbar × 4 sec pressure. |
| Presequence: | 2 min water flush, 2 min 0.1 M NaOH flush, 2 min water flush, 4 min buffer flush. |
| Detector wavelength: | 350/20 nm, ref 214/10 nm |
| Sample solutions: | 1.5% sulfonated HBen-β-CD in water. |

Figure 5:
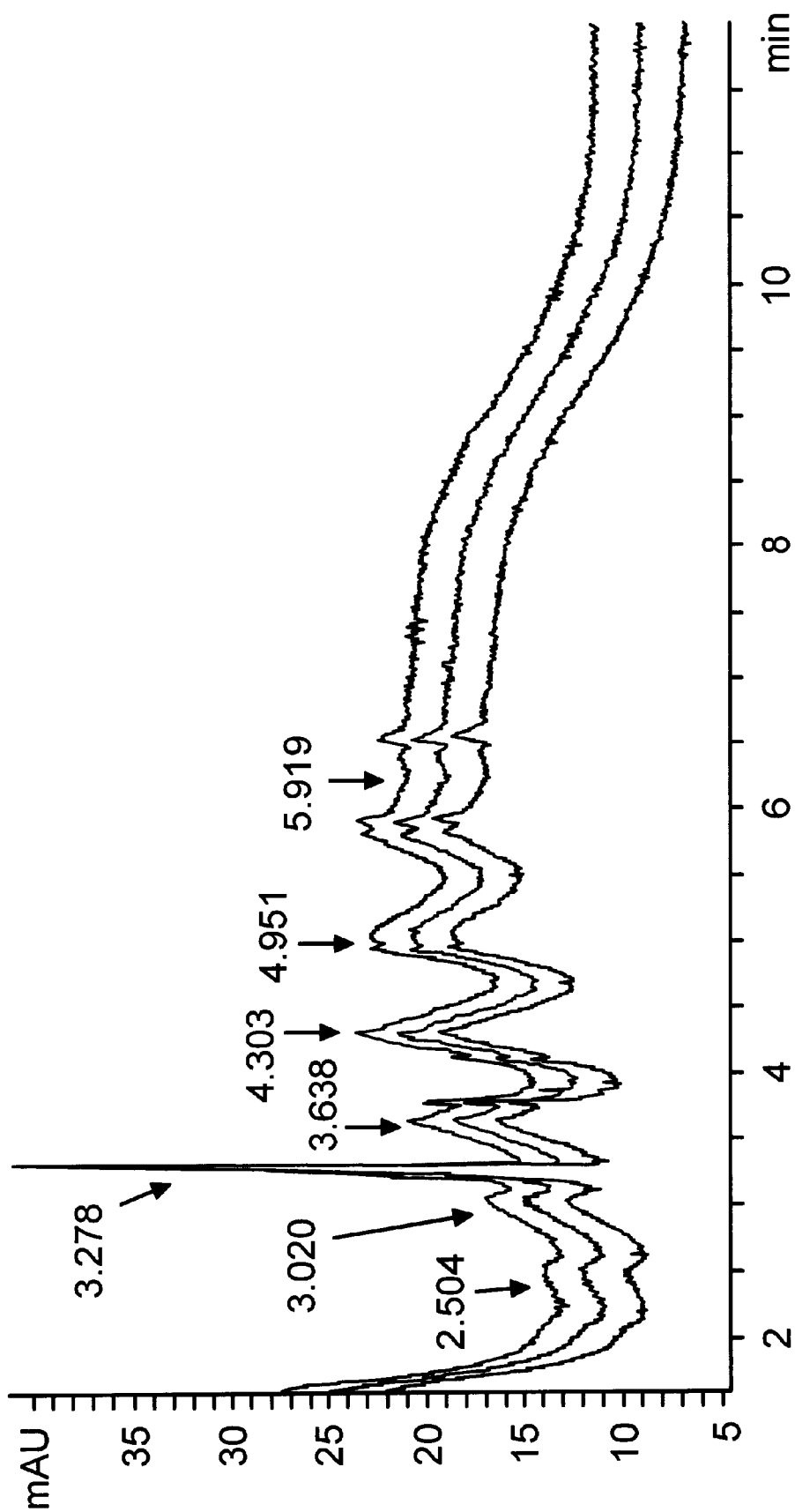
FIG. 5 shows the capillary electrophoresis spectra of sulfonated hydroxybutenyl-β-cyclodextrin. To illustrate reproducibility, the same sample was injected three times.

FIG. 5 shows the capillary electrophoresis spectra collected under the above conditions of sulfonated HBen-β-CD. To illustrate reproducibility, the same sample was injected three times. It is believed that the first fraction consists of all of the sulfonated HBen-β-CD containing one charged sulfonate (cf. Table 6). Above 6 sulfonate groups, the charged isomers migrate as one large group.

TABLE 6

Migration times of sulfonated HBen-β-CD isomers on the basis of sulfonate groups.

| Migration Time (min) | Number of sulfonate groups |
|---|---|
| 2.5 | 1 |
| 3.0 | 2 |
| 3.6 | 3 |
| 4.3 | 4 |
| 4.9 | 5 |
| 5.9 | 6 and over 6 |

This example illustrates that capillary electrophoresis is a suitable method for determining the distribution of charged isomers in sulfonated HBen-β-CD. The example also demonstrates that the sulfonates are randomly distributed.

Example 10
Preparation of Sulfonated HBen-β-CD Prepared from β-CD without Isolation of the HBen-β-CD Intermediate.

To a 1 L glass autoclave was added 125 g (0.11 moles) of β-CD, 1.54 g (0.027 moles) of KOH, and 200 mL of water. The mixture was heated to 100° C. at which time the β-CD dissolved. To this solution was slowly added (8 min) 78 mL (0.97 moles) of 3,4-epoxy-1-butene. The reaction was held at 100° C. for 2 h before cooling to room temperature and adjusting the pH of the reaction mixture to a pH of 7. The autoclave was again pressurized before heating the crude HBen-β-CD solution to 100° C. To the crude HBen-β-CD solution was added 202 g (1.07 moles) of $Na_2S_2O_5$ dissolved in 400 mL of water. The pH of the reaction was allowed to drift. After 4 h 25 min, the reaction was allowed to cool to room temperature. The pH at the end of the reaction was 4.14. In order to evaluate purification by extraction with organic solvents, three 20 mL portions of the crude reaction mixture were removed and extracted 6 times with equal portions of methyl acetate, ethyl acetate, or isopropyl acetate. The water was removed from the SulfoHBen-β-CD samples under vacuum. The organic extracts were also concentrated to dryness under vacuum. All of the samples were analyzed by carbon 13 NMR. This analysis of the material isolated from the organic extracts revealed that they were comprised of 3,4-dihydroxy-1-butene and epoxybutene oligomers. No sodium 3,4-dihydroxybutane-1-sulfonate or cyclodextrin derivatives were found in the organic extract. While all three of the esters were effective in extracting 3,4-dihydroxy-1-butene and epoxybutene oligomers, isopropyl acetate was judged to be the most effective extraction solvent for this purpose. Analysis of white solids obtained from the aqueous layers by carbon 13 NMR revealed that they were comprised of sodium 3,4-dihydroxybutane-1-sulfonate, disodium 3,4-dihydroxybutane-1-sulfonate-2-sulfinate, and the desired sulfonated cyclodextrin. Unreacted olefin was not observed in these samples. The separation of the undesired sodium 3,4-dihydroxybutane-1-sulfonate and disodium 3,4-dihydroxybutane-1-sulfonate-2-sulfinate from the desired sulfonated cyclodextrin was examined using the sample obtained from the isopropyl acetate extraction. The methods of separation examined were dialysis (500 and 1000 MWCO) and nanofiltration (500 MWCO cellulose acetate membrane, vide infra). Little if any separation was obtained with the 500 MWCO dialysis bag. Nanofiltration (500 MWCO) removed sodium 3,4-dihydroxybutane-1-sulfonate from the sulfonated cyclodextrin. However, the sulfonated cyclodextrin still contained a significant amount of disodium 3,4-dihydroxybutane-1-sulfonate-2-sulfinate. In contrast, with the 1000 MWCO dialysis bag, both sodium 3,4-dihydroxybutane-1-sulfonate and disodium 3,4-dihydroxybutane-1-sulfonate-2-sulfinate were separated from the sulfonated cyclodextrin. Analysis of the purified sulfonated cyclodextrin by electrospray mass spectrometry indicated that the derivative has a total MS of 5.67 comprised of $Sulfo_{2.54}Sulfin_{0.6}HBen_{2.53}$-β-CD.

This example illustrates that, because of the common reaction media, the sulfonated cyclodextrin of this invention can be prepared in a one-pot reaction without isolation of the HBen-β-CD intermediate. The example illustrates that acetate esters are effective solvents in extracting 3,4-dihydroxy-1-butene and epoxybutene oligomers. Finally, this example indicates that the reaction by-products, sodium 3,4-dihydroxybutane-1-sulfonate and disodium 3,4-dihydroxybutane-1-sulfonate-2-sulfinate, can be separated from the desired sulfonated cyclodextrin by techniques such as dialysis or nanofiltration provided the membrane has a molecular weight cutoff of about 1000. The results also suggest that it may be advantageous to remove the 3,4-dihydroxy-1-butene by-product by a technique such as nanofiltration prior to sulfonation of the HBen-β-CD.

Example 11
Purification of HBen-β-CD to Remove 3,4-dihydroxy-1-butene by Nanofiltration.

Figure 6:
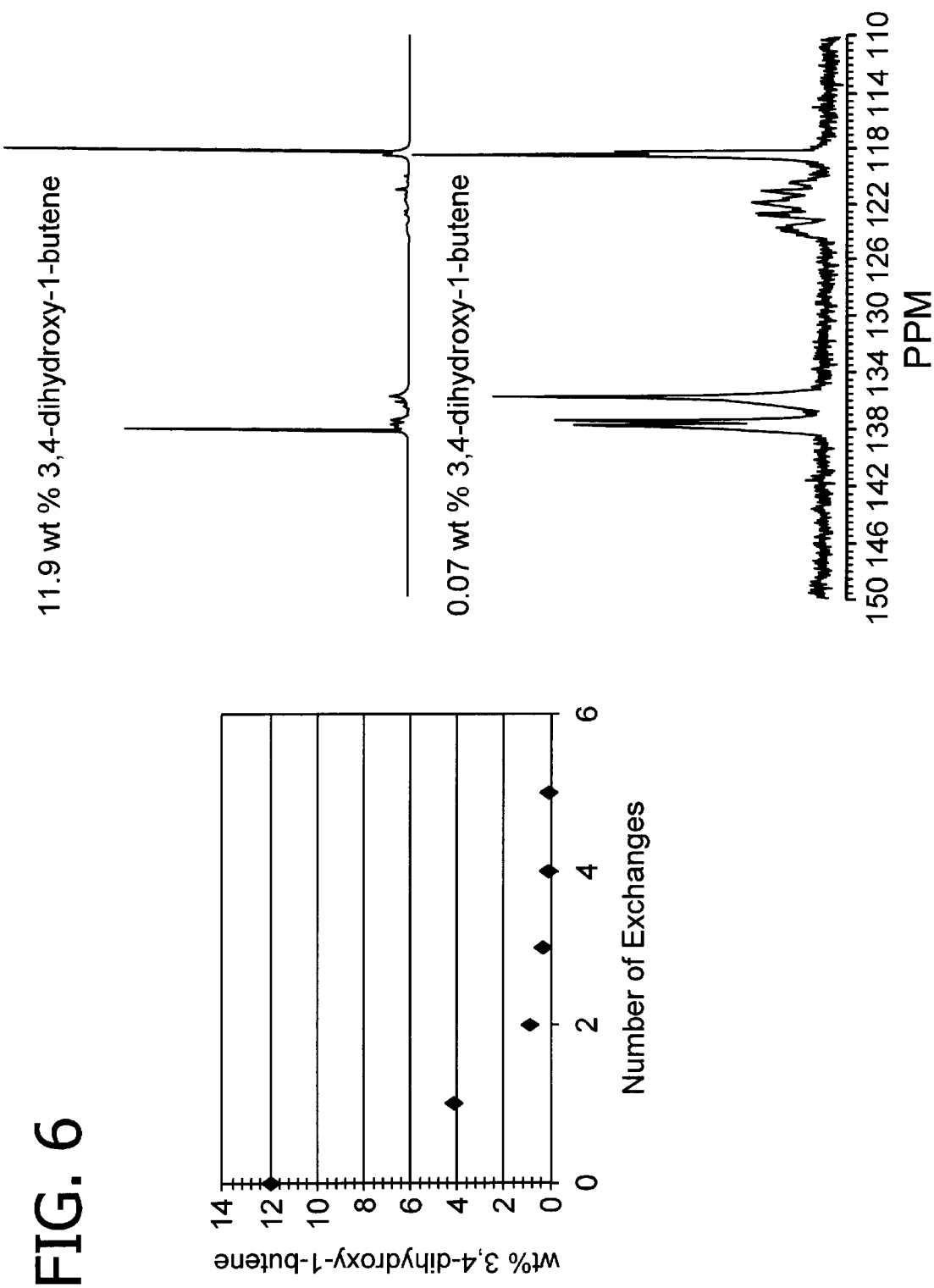
FIG. 6 shows (a) the removal of 3,4-dihydroxy-1-butene from HBen-β-CD by nanofiltration and (b) the carbon 13 NMR (125 MHz) spectra of the olefinic resonances before and after nanofiltration.

Because of excess 3,4-dihydroxy-1-butene generated in the preparation of the intermediate hydroxybutenyl cyclodextrin which can lead to an increased use of $Na_2S_2O_5$ and more difficult late stage purifications, it may be preferred that residual 3,4-dihydroxy-1-butene is removed from hydroxybutenyl cyclodextrin prior to conversion to sulfonated hydroxybutenyl cyclodextrin. To demonstrate the removal of residual 3,4-dihydroxy-1-butene from HBen-β-CD, a sample of HBen-β-CD having an initial concentration of 3,4-dihydroxy-1-butene of 11.9 wt % was subjected to nanofiltration. A 200 mL nanofiltration flask with a 63.5 mm cellulose acetate membrane (500 molecular weight cut off) was charged with a solution of 5 g of HBen-β-CD in 60 mL of deionized water. The flask was pressurized with 70 psi $N_2$. The sample was concentrated to approximately 25 wt % solids, which was considered to be one solvent exchange. Five samples were processed in this manner where the samples received from 1 to 5 exchanges. The results are summarized in FIG. 6.

This example demonstrates that nanofiltration of an aqueous solution of hydroxybutenyl cyclodextrin through a 500 MWCO membrane is a quick and efficient means for removing 3,4-dihydroxy-1-butene and other components, including salts, that have a molecular weight of less than about 500.

Example 12
Preparation of Sulfonated HBen-β-CD from HBen-β-CD with a Low 3,4-dihydroxy-1-butene Content at a Controlled pH of 7.3.

Figure 7:
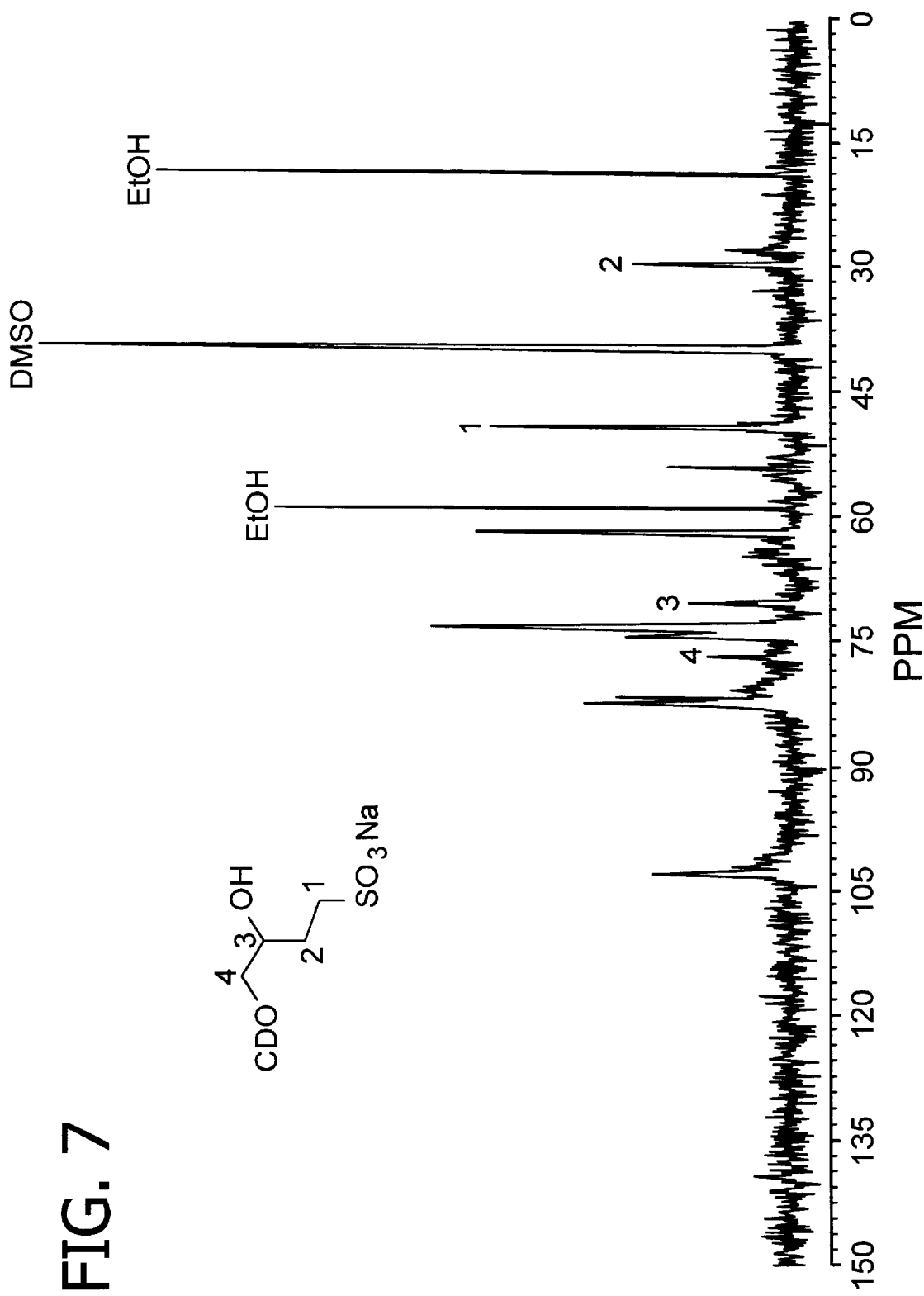
FIG. 7 shows the 125 MHz carbon 13 NMR spectra (125 MHz) of a sulfonated HBen-β-CD.
Figure 8:
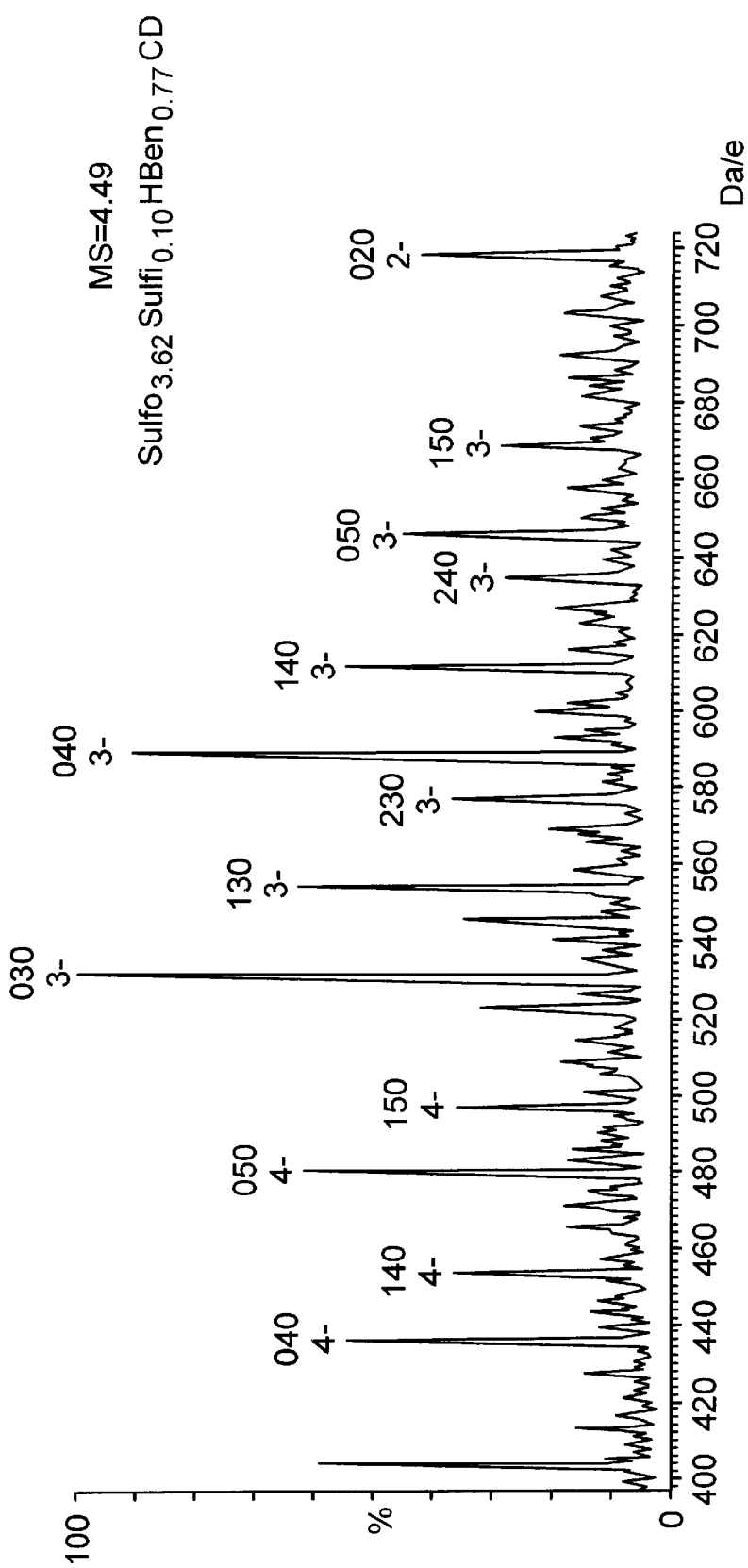
FIG. 8 shows a portion of the electrospray mass spectrum for a sulfonated HBen-β-CD.

In a 15 mL one-neck round bottom flask, 1.5 g of HBen-β-CD was dissolved in 3 mL of deionized water. The HBen-β-CD had a MS of 4.54 and contained 0.35 wt % 3,4-dihydroxy-1-butene. The flask was placed in a preheated 75° C. oil bath. A second solution was prepared by dissolving 1.14 g of $Na_2S_2O_5$ in 2 mL of deionized water. The pH of the $Na_2S_2O_5$ solution was adjusted from 5.4 to 7.3 prior to adding this solution to the HBen-β-CD solution. During the course of the reaction, the reaction pH was maintained at 7.3. After 4 h 20 min, the reaction was removed from the oil bath and concentrated in vacuo, which provided 3.1 g of a white solid. Carbon 13 NMR ($D_2O$) of the crude product showed nearly complete disappearance of the olefin and formation of sulfonate with minimal formation of the sulfinate (FIG. 7). In order to determine the MS, the sample was analyzed by electrospray mass spectrometry. The resulting mass spectrum is shown in FIG. 8. Analysis of this spectrum revealed that sample has had a total MS of 4.49 comprised of $Sulfo_{3.62}Sulfin_{0.10}HBen_{0.77}CD$.

This example illustrates that HBen-β-CD which has been treated to remove 3,4-dihydroxy-1-butene, can be easily sulfonated at a controlled pH with minimal formation of the sulfinate.

Example 13
Preparation of Hydroxybutenyl Cellulose.

Cellulose (wood pulp, 20 g) was added to a mixture of 2 g NaOH, 200 mL of t-BuOH, and 28 mL of water. The mixture was rolled for 1 h then filtered to obtain 46 g of a wet cellulose cake. The alkaline cellulose was added to a 1 L glass pressure reactor along with 190 mL of hexane and 82 mL of 3,4-epoxy-1-butene. The vessel was flushed with $N_2$ and pressurized to 1 bar. The reaction mixture was heated to 130° C. at which time the pressure reached 6.5 bar. After 6 h, the pressure had dropped to 5.6 bar and the cellulose was dispersed as a gel in hexane. The reaction was allowed to cool to room temperature and neutralized with acetic acid. The hexane was removed by filtration and the reaction product was taken up in hot water, which was placed in a steam bath. After 30 min at 90° C., the reaction product was isolated by filtration and washed with 90° C. water. After drying, 38.3 g of product was obtained which was soluble in solvents such as DMSO. Hydroxybutenyl cellulose can be sulfonated by the methods described above.

This example demonstrates that other polysaccharides such as cellulose, starch, hemicellulose, cellulose derivatives, and alkylpolyglycosides can react with 3,4-epoxy-1-butene to form products suitable for sulfonation by the methods previously described in this invention.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A cyclodextrin ether comprising at least one hydroxybutyl sulfonate substituent.

2. A cyclodextrin ether comprising at least one hydroxybutyl sulfonate sulfinate substituent.

3. A cyclodextrin ether comprising at least one hydroxybutyl disulfonate substituent.

4. A cyclodextrin ether comprising at least one R substituent and at least one hydroxybutyl sulfonate substituent, wherein R is derived from an O-alkylating agent other than 3,4-epoxy-1-butene.

5. A cyclodextrin ether comprising at least one R substituent and at least one hydroxybutyl sulfonate sulfinate substituent, wherein R is derived from an O-alkylating agent other than 3,4-epoxy-1-butene.

6. A cyclodextrin ether comprising at least one R substituent and at least one hydroxybutyl disulfonate substituent, wherein R is derived from an O-alkylating agent other than 3,4-epoxy-1-butene.

7. A water-soluble or water dispersible cyclodextrin ether host molecule comprising at least one substituent selected from the group consisting of hydroxybutyl sulfonate, hydroxybutyl sulfonate sulfinate, and hydroxylbutyl disulfonate, wherein the cyclodextrin ether host molecule before being sulfonated, sulfonated and sulfinated, or disulfonated has a total DS of hydroxybutenyl from about 0.02 to about 9.0 and is capable of forming host-guest complexes.

8. A water-soluble or water dispersible cyclodextrin ether host molecule comprising at least one R substituent and at least one substituent selected from the group consisting of hydroxybutyl sulfonate, hydroxybutyl sulfonate sulfinate, and hydroxylbutyl disulfonate, wherein R is derived from an O-alkylating agent other than 3,4-epoxy-1-butene, and wherein the cyclodextrin host molecule before being sulfonated, sulfonated and sulfinated, or disulfonated has a total DS of hydroxybutenyl from about 0.02 to about 9.0 and is capable of forming host-guest complexes.

9. A process for making a cyclodextrin ether comprising at least one substituent selected from the group consisting of hydroxybutyl sulfonate, hydroxybutyl sulfonate sulfinate, and hydroxylbutyl disulfonate, said process comprising the step of contacting hydroxybutenyl cyclodextrin with a source of bisulfite and optionally with hydrogen peroxide or sodium hypochlorite.

10. A process for making a cyclodextrin ether comprising at least one R substituent and at least one substituent selected from the group consisting of hydroxybutyl sulfonate, hydroxybutyl sulfonate sulfinate, and hydroxylbutyl disulfonate, wherein R is derived from an O-alkylating agent other than 3,4-epoxy-1-butene, said process comprising the step of contacting hydroxybutenyl cyclodextrin comprising at least one R substituent with a source of bisulfite and optionally with hydrogen peroxide or sodium hypochlorite.

11. A process for making a sulfonated, sulfonated and sulfinated, or disulfonated cyclodextrin ether, wherein the cyclodextrin ether comprises at least one 2-hydroxybutenyl substituent, said process comprising the step of contacting a cyclodextrin ether comprising 2-hydroxybutenyl substituents with a source of bisulfite and optionally with hydrogen peroxide or sodium hypochlorite.

12. A process for making a sulfonated, sulfonated and sulfinated, or disulfonated cyclodextrin ether from a cyclodextrin ether, comprising at least one R substituent and at least one 2-hydroxybutenyl substituent, wherein R is derived from an O-alkylating agent other than 3,4-epoxy-1-butene, said process comprising the step of contacting said cyclodextrin ether comprising at least one R substituent and at least one 2-hydroxybutenyl substituent with a source of bisulfite and optionally with hydrogen peroxide or sodium hypochlorite.

13. An inclusion complex comprising a water-soluble or water dispersible cyclodextrin ether host molecule and an included material, wherein the cyclodextrin ether comprises at least one substituent selected from the group consisting of hydroxybutyl sulfonate, hydroxybutyl sulfonate sulfinate, and hydroxylbutyl disulfonate, and wherein the cyclodextrin ether host molecule before being sulfonated, sulfonated and sulfinated, or disulfonated has a total DS of hydroxybutenyl from about 0.02 to about 9.0.

14. An inclusion complex comprising a water-soluble or water dispersible cyclodextrin ether host molecule and an included material, wherein the cyclodextrin ether host molecule comprises at least one R substituent and at least one substituent selected from the group consisting of hydroxybutyl sulfonate, hydroxybutyl sulfonate sulfinate, and hydroxylbutyl disulfonate, wherein R is derived from an O-alkylating agent other than 3,4-epoxy-1-butene, and wherein the cyclodextrin ether host molecule before being sulfonated, sulfonated and sulfinated, or disulfonated has a total DS of hydroxybutenyl from about 0.02 to about 9.0.

* * * * *